US 6,716,866 B2
McMinn et al.
(45) Date of Patent: Apr. 6, 2004

(54) ARYL-BENZIMIDAZOLE COMPOUNDS HAVING ANTIINFECTIVE ACTIVITY

(75) Inventors: Dustin L. McMinn, So. San Francisco, CA (US); Roland W. Bürli, San Francisco, CA (US); Jacob Kaizerman, Redwood City, CA (US); Eldon E. Baird, Half Moon Bay, CA (US); Matthew J. Taylor, San Francisco, CA (US)

(73) Assignee: GeneSoft Pharmaceuticals, Inc., So. San Francisco, CA (US)

( * ) Notice: Subject to any disclaimer, the term of this patent is extended or adjusted under 35 U.S.C. 154(b) by 0 days.

(21) Appl. No.: 10/165,433

(22) Filed: Jun. 6, 2002

(65) Prior Publication Data

US 2003/0191168 A1 Oct. 9, 2003

Related U.S. Application Data

(60) Provisional application No. 60/298,206, filed on Jun. 13, 2001, provisional application No. 60/325,134, filed on Sep. 24, 2001, provisional application No. 60/333,830, filed on Nov. 27, 2001, and provisional application No. 60/342,309, filed on Dec. 21, 2001.

(51) Int. Cl.[7] ............... C07D 417/12; A61K 31/418
(52) U.S. Cl. ............... 514/387; 544/139; 548/181; 548/304.7
(58) Field of Search ............... 544/139; 548/181, 548/304.7; 514/387

(56) References Cited

U.S. PATENT DOCUMENTS

| | | | |
|---|---|---|---|
| 5,698,674 A | 12/1997 | Bruice et al. | |
| 5,808,087 A | 9/1998 | Matsunaga et al. | |
| 5,821,258 A | 10/1998 | Matsunaga | |
| 5,852,011 A | 12/1998 | Matsunaga | |
| 5,998,140 A | 12/1999 | Dervan et al. | |
| 6,090,947 A | 7/2000 | Dervan et al. | |
| 6,153,642 A | 11/2000 | Cozzi et al. | |

FOREIGN PATENT DOCUMENTS

| | | |
|---|---|---|
| DE | 19920936 A1 | 11/2000 |
| JP | 08027146 A2 | 1/1996 |
| JP | 11171886 A | 6/1999 |
| JP | 11189594 A | 7/1999 |
| WO | WO 98/35702 A1 | 8/1998 |
| WO | WO 98/37066 A1 | 8/1998 |
| WO | WO 98/37067 A1 | 8/1998 |
| WO | WO 98/37087 A1 | 8/1998 |
| WO | WO 98/45284 A1 | 10/1998 |
| WO | WO 98/49142 A1 | 11/1998 |
| WO | WO 98/50582 A1 | 11/1998 |
| WO | WO 98/52614 A2 | 11/1998 |
| WO | WO 99/50266 A2 | 10/1999 |
| WO | WO 00/15209 A2 | 3/2000 |
| WO | WO 00/15773 A2 | 3/2000 |
| WO | WO 01/19792 A1 | 3/2001 |

OTHER PUBLICATIONS

Baird et al., "Solid Phase Synthesis of Polyamides Containing Imidazole and Pyrrole Amino Acids," *J. Am. Chem. Soc.*, 118:6141–6146 (1996).
Baraldi et al., "Synthesis and Antitumor Activity of New Benzoheterocyclic Derivatives of Distamycin A," *J. Med. Chem.* 43:2675–2684 (2000).
Boger et al., "Total Synthesis of Distamycin A and 2640 Analogues: A Solution–Phase Combinatorial Approach to the Discovery of New Bioactive DNA Binding Agents and Development of a Rapid High–Throughput Screen for Determining Relative DNA Binding Affinity of DNA Binding Sequence Selectivity," *J. Am. Chem. Soc.* 122:6382–6394 (2000).
Floreancig et al., "Recognition of the Minor Groove of DNA by Hairpin Polyamides Containing α–Susbstituted–β–Amino Acids," *J. Am. Chem. Soc.* 122:6342–6350 (2000).
Khalaf et al., "The Synthesis of Some Head to Head Linked DNA Minor Groove Binders," *Tetrahedron 56* (2000) 5225–5239.
Matsuba et al., "A Novel Synthetic DNA Minor Groove Binder, MS–247:AntiTumor Activity and Cytotoxic Mechanism," *Cancer Chemo. Pharm.* 46: 1–9 (2000).
Trauger et al., "Recognition of DNA By Designed Ligands At Subnanomolar Concentrations," *Nature,* 382: 559–561 (1996).

*Primary Examiner*—Robert Gerstl
(74) *Attorney, Agent, or Firm*—Townsend and Townsend and Crew LLP

(57) ABSTRACT

Aryl-benzimidazole compounds according to the formula where $Ar^1$, $R^1$, $R^2$, Y, W, and N are as defined herein, bind to DNA and have antibacterial activity.

42 Claims, 7 Drawing Sheets

(I-1)

(I-2)

(I-3)

(I-4)

(I-5)

(I-6)

(I-7)

(I-8)

(I-9)

(I-10)

(I-11)

(I-12)

(I-13)

(I-14)

(I-15)

(I-16)

(I-17)

(I-18)

(I-19)

(I-20)

(I-21)

(I-22)

(I-23)

(I-24)

(I-25)

(I-26)

(I-27)

(I-28)

(I-29)

(I-30)

(I-31)

(I-32)

(I-33)

(I-34)

(I-35)

(I-36)

(I-37)

(I-38)

(I-39)

(I-40)

ARYL-BENZIMIDAZOLE COMPOUNDS HAVING ANTIINFECTIVE ACTIVITY

CROSS-REFERENCE TO RELATED APPLICATIONS

Figure 1A:
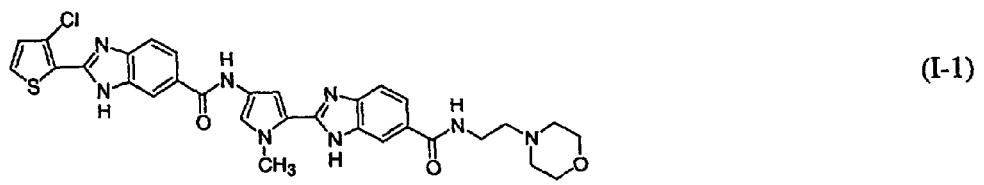
Figure 1A:
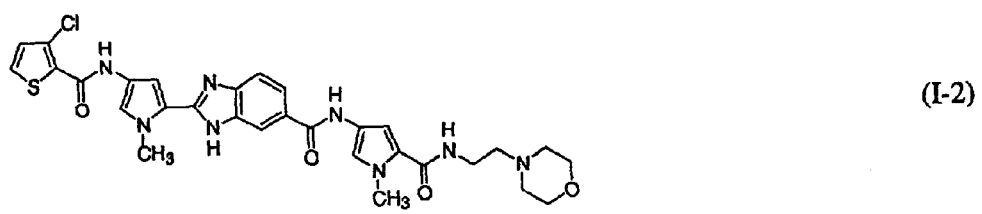
Figure 1A:
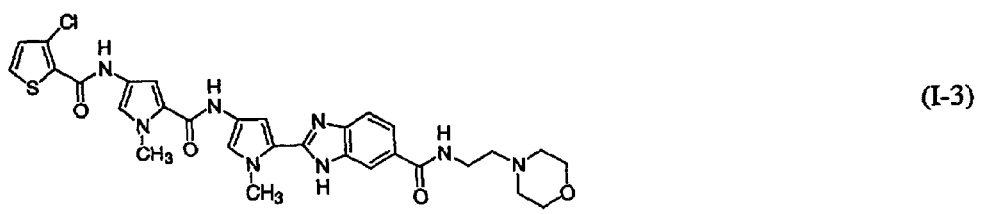
Figure 1A:
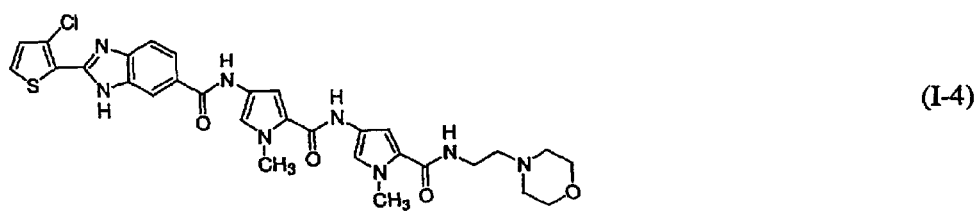
Figure 1A:
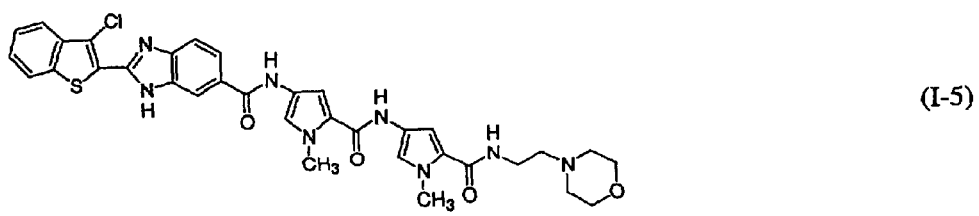
Figure 1A:
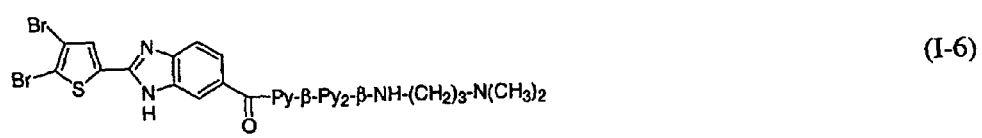
Figure 1A:
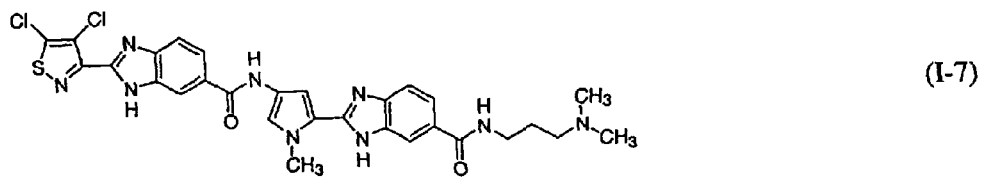

This application claims the benefit of U.S. Ser. Nos. 60/298,206, filed Jun. 13, 2001; 60/325,134, filed Sep. 24, 2001; 60/333,830, filed Nov. 27, 2001; and 60/342,309, filed Dec. 21, 2001; the disclosures of which are incorporated herein by reference.

STATEMENT REGARDING FEDERALLY SPONSORED RESEARCH OR DEVELOPMENT

This invention was made with Government support under Grant No. N65236-99-1-5427 awarded by the Space and Naval Warfare Systems Command. The Government has certain rights in this invention.

BACKGROUND OF THE INVENTION

1. Field of the Invention

This invention relates to compounds having an aryl-benzimidazole structural element, in particular ones binding to nucleic acids and having anti-bacterial properties, and methods for their use.

2. Description of Related Art

A number of naturally occurring or synthetic compounds bind to double stranded nucleic acid, especially double stranded DNA ("dsDNA"). Some bind to the major groove, while others bind to the minor groove. Still others intercalate between adjacent base pairs. Combination binding modes are known, in which a compound has binding interactions with more than one nucleic acid site.

It has been proposed to use dsDNA binding compounds to regulate the expression of genes for medical purposes. If a disease is characterized by the overexpression or undesired expression of a gene (e.g., an oncogene), in principle the disease can be treated by suppressing wholly or partially the gene's expression via the binding of a compound to the gene or a promoter site thereof and interfering with transcription. Infections by pathogens such as fungi, bacteria, and viruses can be treated with compounds that affect the expression of genes essential for the pathogen's proliferation. Or, in a disease characterized by non- or under-expression of a beneficial gene, the expression of the beneficial gene can be up-regulated with a compound that binds to the binding site of a repressor.

The natural products distamycin and netropsin represent a class of DNA-binding compounds that has been studied over the years:

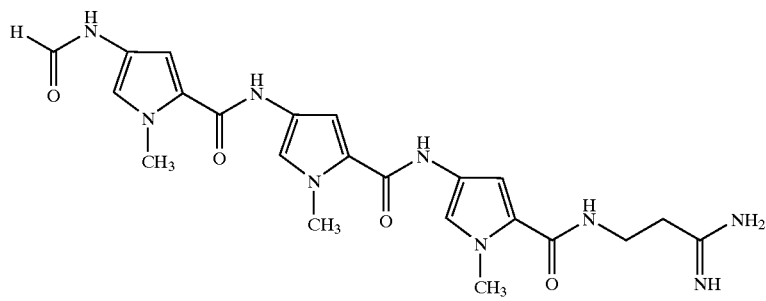

Distamycin

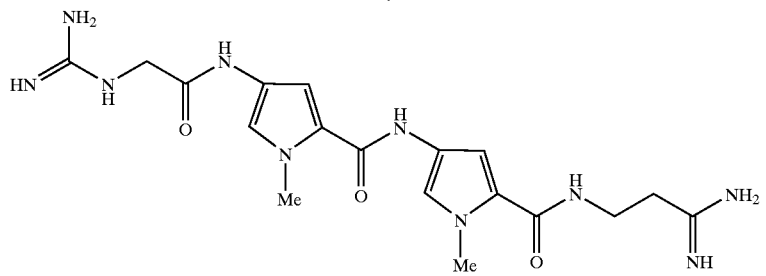

Netropsin

Structurally, distamycin and netropsin may be viewed as heteroaromatic polyamides, having as their core structural motif N-methylpyrrole carboxamide residues. They bind to the minor groove, their crescent molecular shapes providing a conformational fit within the groove. The binding occurs with a preference for A,T rich dsDNA tracts.

A number of analogs of distamycin or netropsin have been synthesized, with the objective of enhancing or varying biological properties, increasing binding affinity to dsDNA, and/or improving specificity in base pair sequence recognition. Examples include Matsunaga et al., U.S. Pat. Nos. 5,808,087 (1998), 5,821,258 (1998), 5,852,011 (1998); JP 11-171886; and JP 11-89594.

BRIEF SUMMARY OF THE INVENTION

This invention provides aryl-benzimidazole compound having the formula

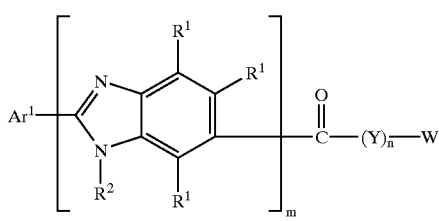

(I)

and pharmaceutically acceptable salts thereof.

$Ar^1$ is a substituted or unsubstituted phenyl, naphthyl, 5-member heteroaromatic, 6-member heteroaromatic, or fused ring heteroaromatic group.

Subscript m is 0 or 1, while subscript n is an integer from 1 to 25, inclusive, with the proviso that if m is 0, then at least one moiety Y is a moiety $M^4$ and n is at least 2.

Each moiety Y is independently selected from the group consisting of (a) moieties $M^1$ having the formula

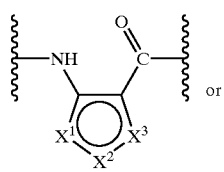

(IIa)

or

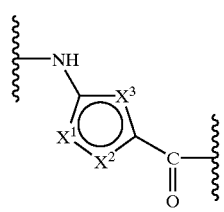

(IIb)

wherein
one of $X^1$, $X^2$, and $X^3$ is a ring vertex selected from the group consisting of —O—, —S—, and —NR²—, and the other two of $X^1$, $X^2$, and $X^3$ are ring vertices selected from the group consisting of =N— and =CR¹—;

(b) moieties $M^2$ having the formula

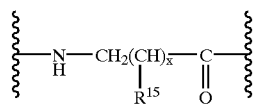

(III)

wherein
x is 0 or 1 and
each $R^{15}$ is independently H, OH, NH₂, or F;

(c) moieties $M^3$ having the formula

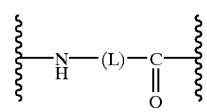

(IV)

wherein each L is independently a divalent moiety separating —NH— and —(C=O)— by 3 or 4 atoms; and (d) moieties $M^4$ having the formula

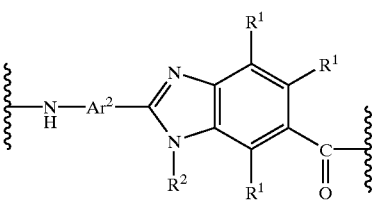

(V)

wherein each $Ar^2$ is independently selected from the group consisting of

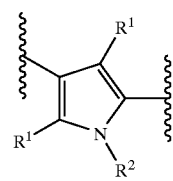

(VIa)

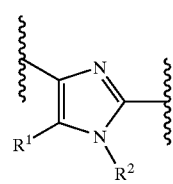

(VIb)

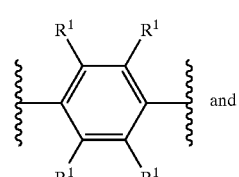

(VIc)

and

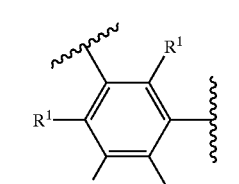

(VId)

W is $N(R^2)_2$ or $OR^2$.

In the preceding formulae each $R^1$ is independently H, F, Cl, Br, I, CN, OH, NO₂, NH₂, a substituted or unsubstituted $(C_1-C_{12})$alkyl group, or a substituted or unsubstituted $(C_1-C_{12})$heteroalkyl group; and each $R^2$ is independently H, a substituted or unsubstituted $(C_1-C_{12})$alkyl group, or a substituted or unsubstituted $(C_1-C_{12})$heteroalkyl group.

Preferably, $R^1$ is H, halogen (F, Cl, Br, or I), a $(C_1-C_5)$ alkyl group such as methyl, ethyl, propyl, isopropyl, butyl, isobutyl, s-butyl, pentyl, and the like, a $(C_1-C_5)$alkoxy group such as methoxy, ethoxy, propoxy, isopropoxy, butoxy, and the like, hydroxy, or cyano. Preferably, each $R^2$ is H or a $(C_1-C_5)$alkyl group such as methyl, ethyl, propyl, isopropyl, butyl, isobutyl, s-butyl, pentyl, and the like.

BRIEF DESCRIPTION OF THE DRAWING(S)

Figure 1B:
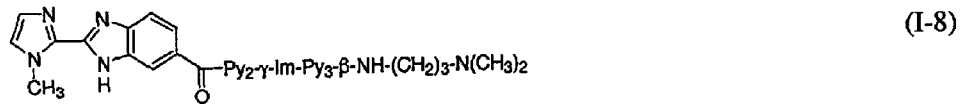
Figure 1B:
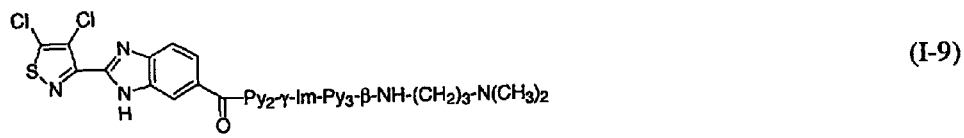
Figure 1B:
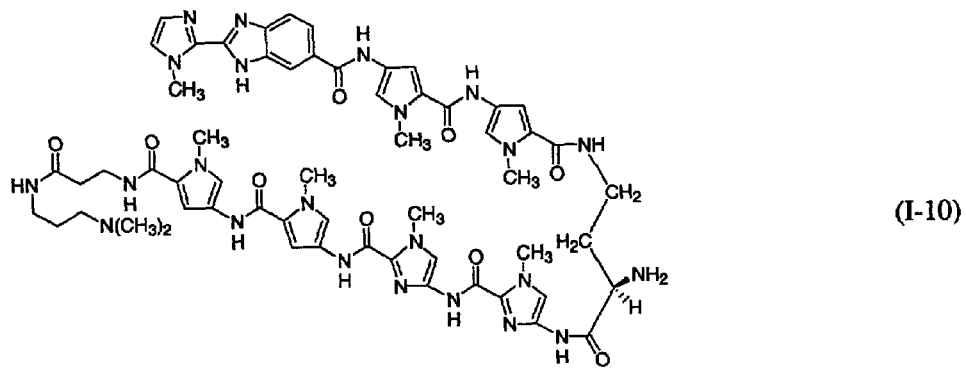
Figure 1B:
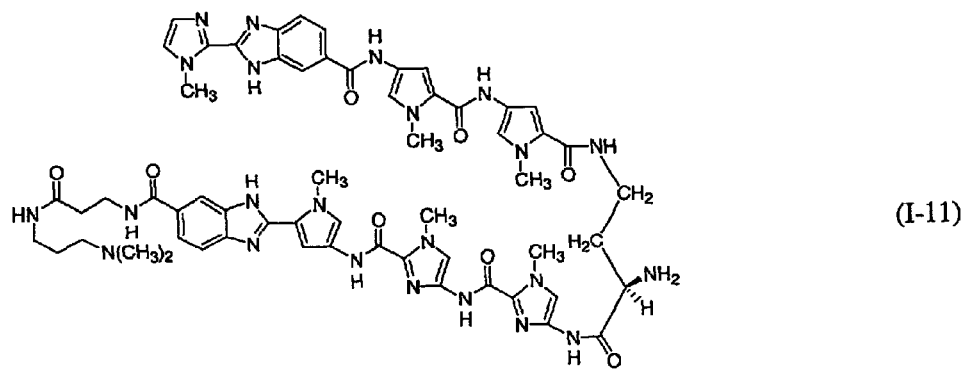
Figure 1B:
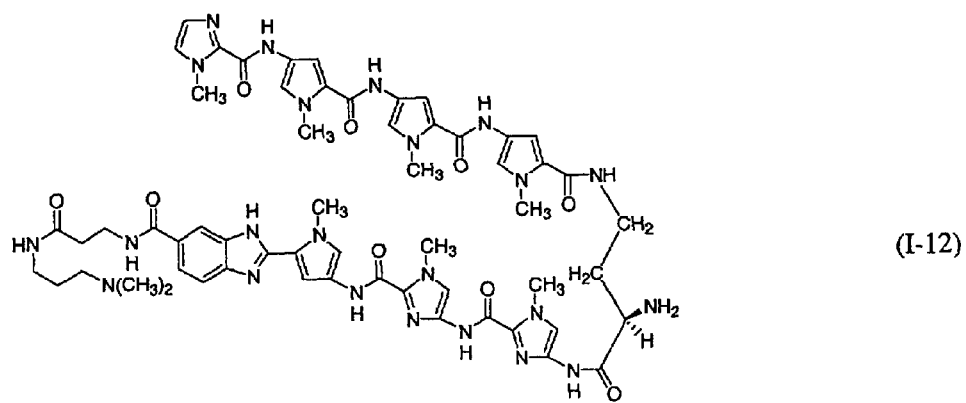
Figure 1C:
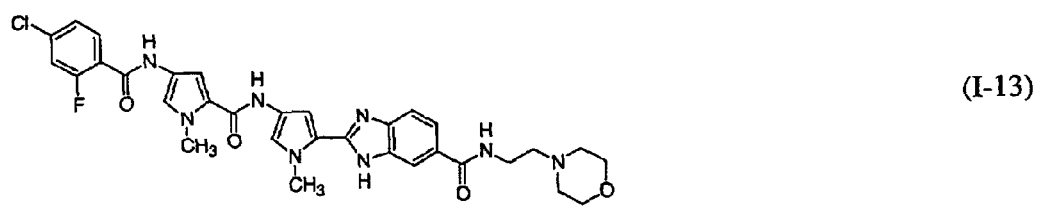
Figure 1C:
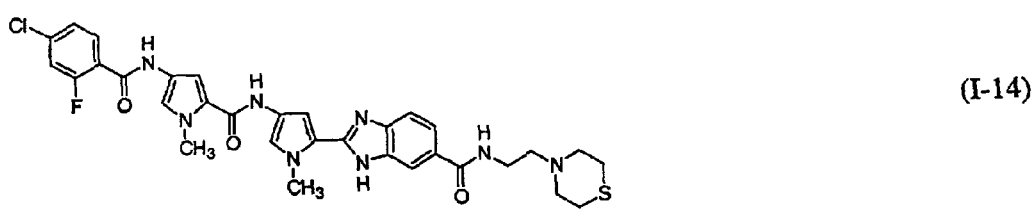
Figure 1C:
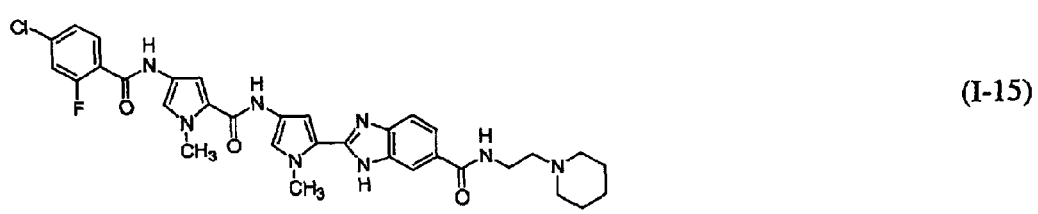
Figure 1C:
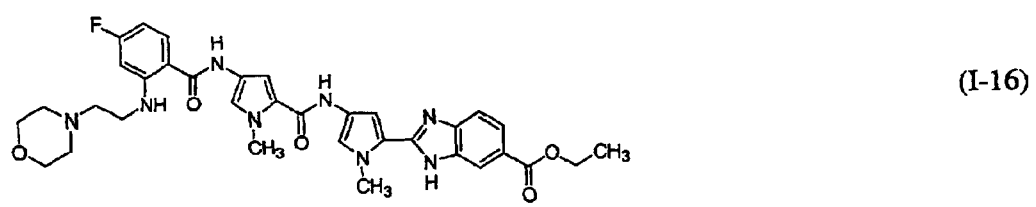
Figure 1C:
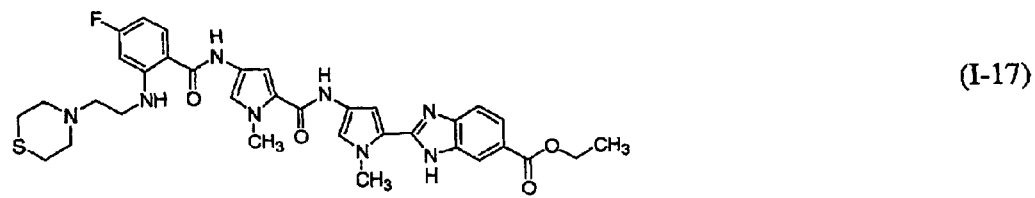
Figure 1C:
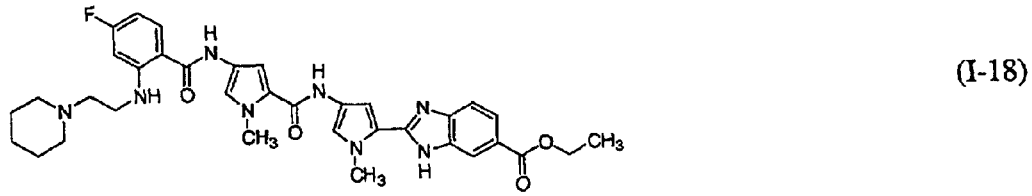
Figure 1D:
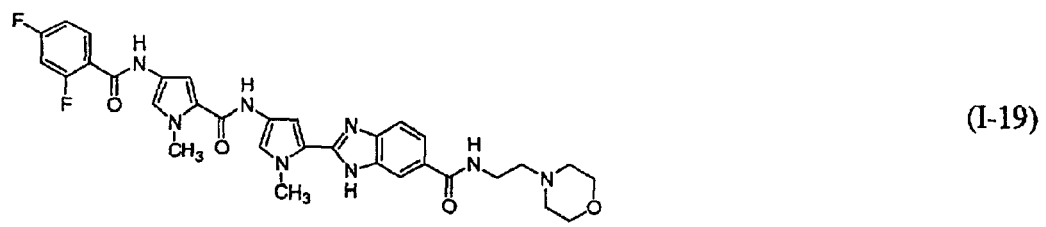
Figure 1D:
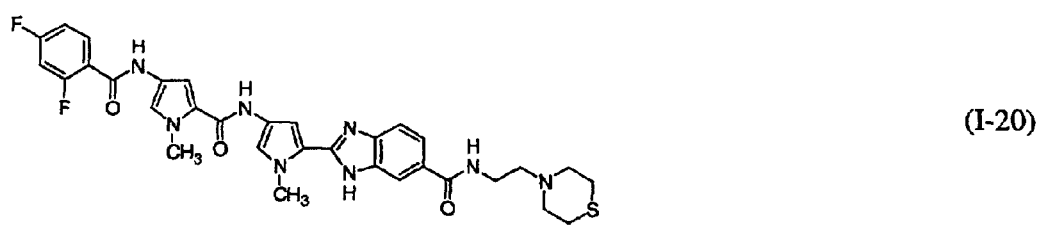
Figure 1D:
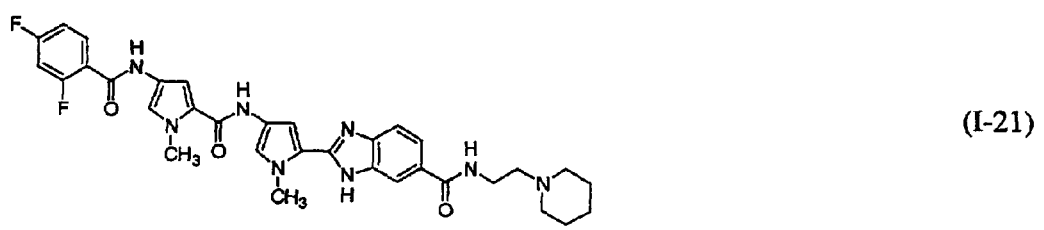
Figure 1D:
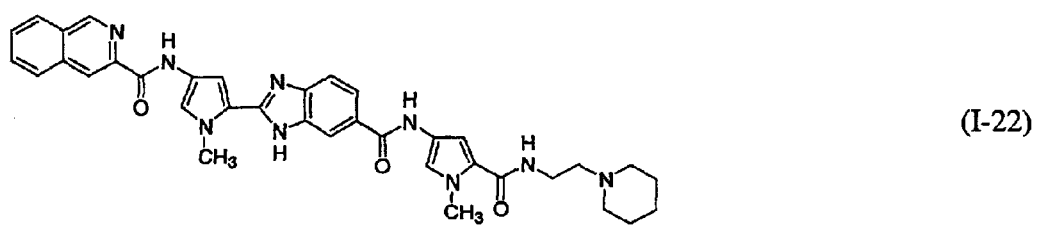
Figure 1D:
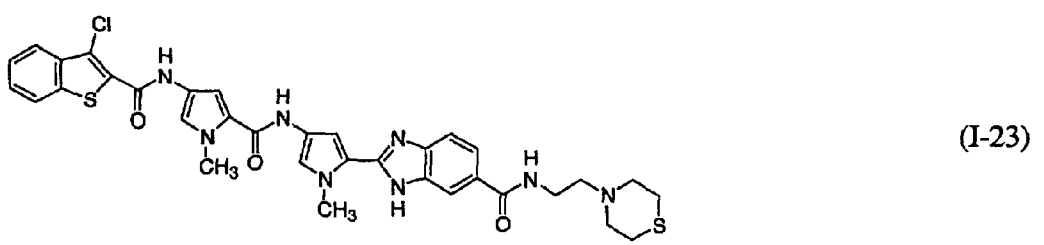
Figure 1D:
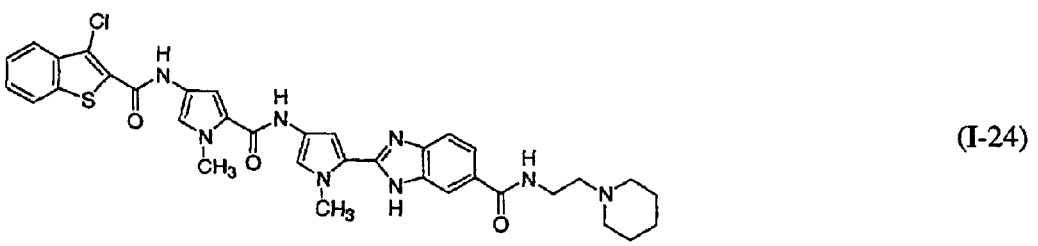
Figure 1E:
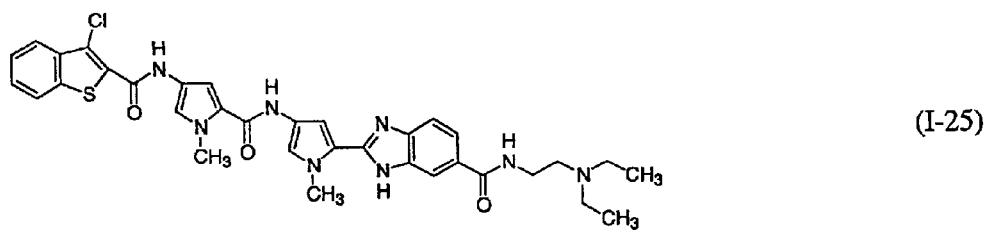
Figure 1E:
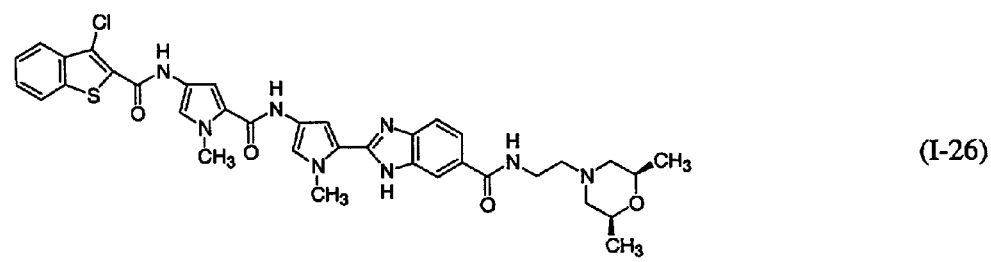
Figure 1E:
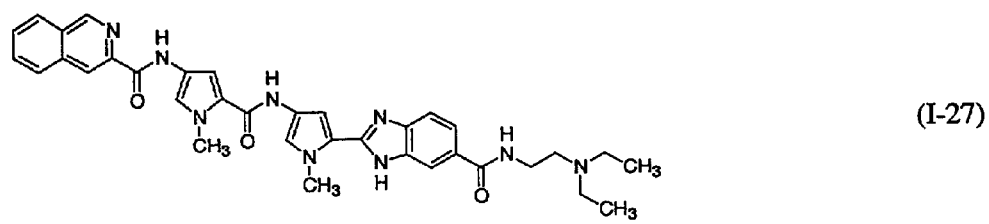
Figure 1E:
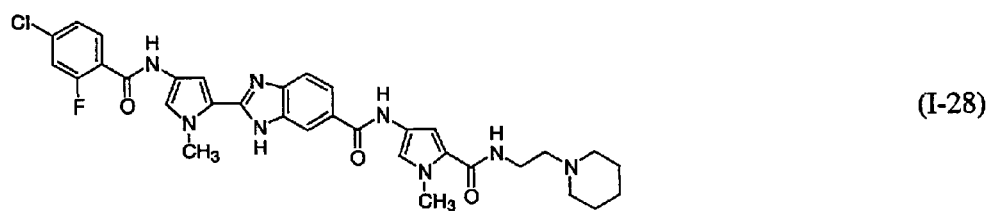
Figure 1E:
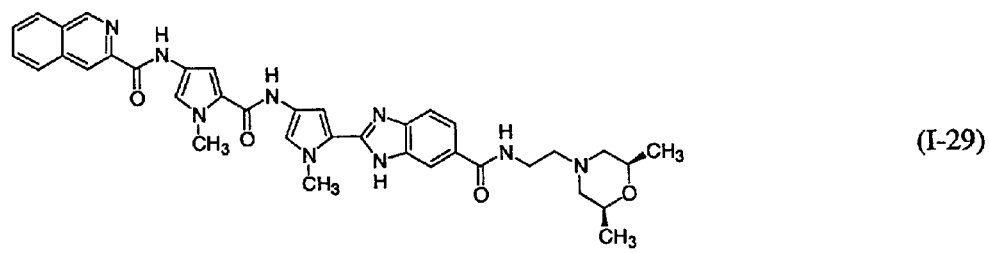
Figure 1E:
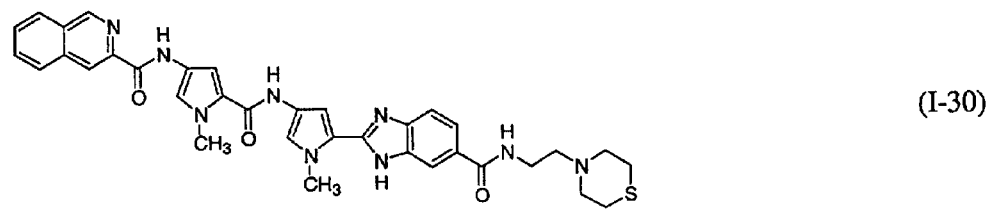
Figure 1F:
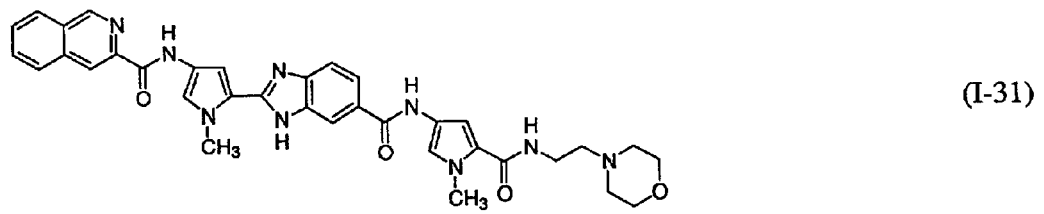
Figure 1F:
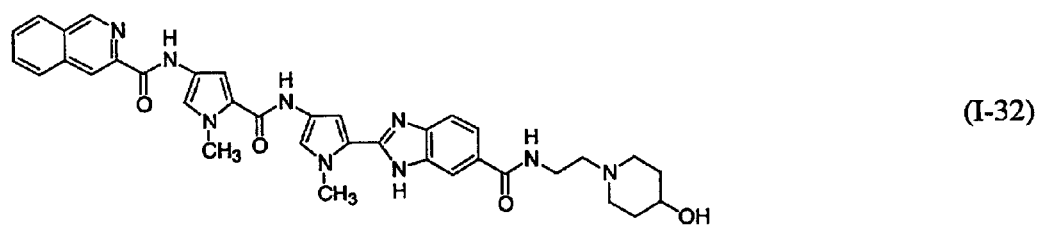
Figure 1F:
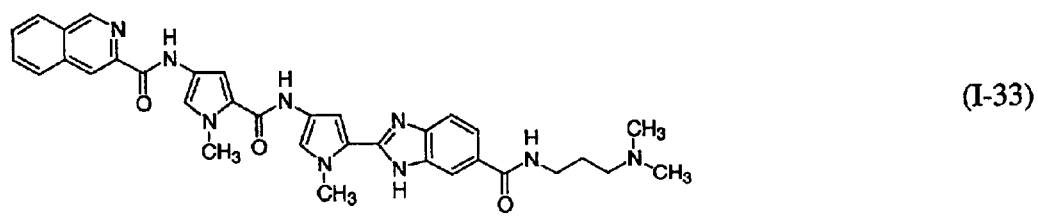
Figure 1F:
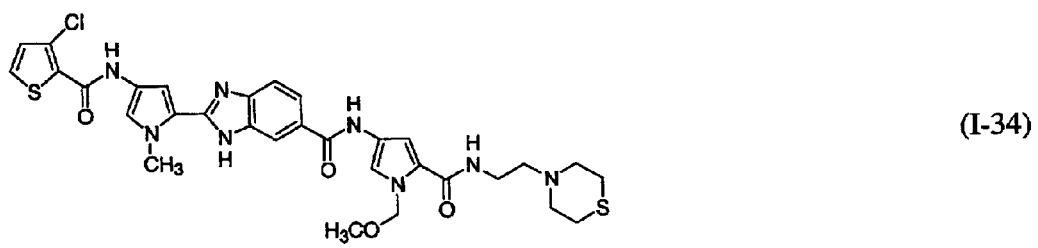
Figure 1F:
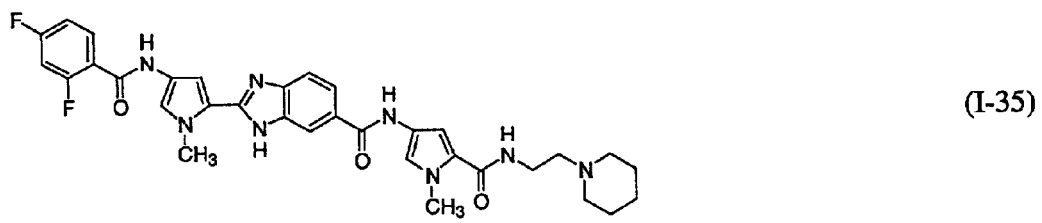
Figure 1F:
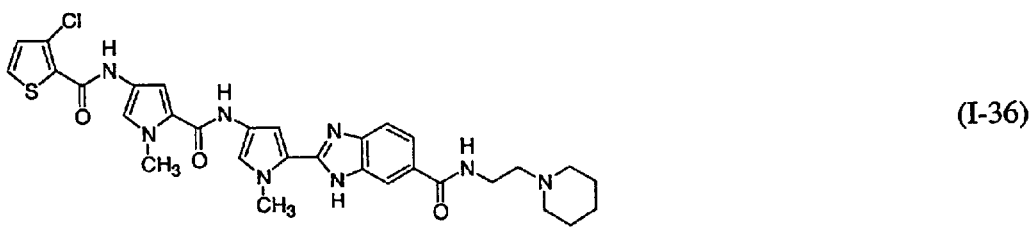
Figure 1G:
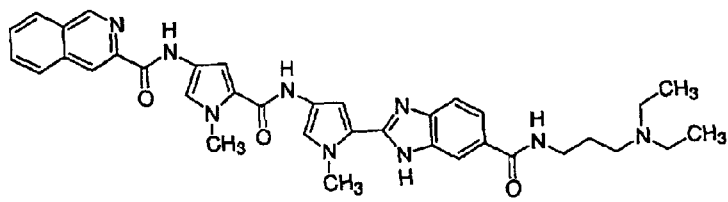
Figure 1G:
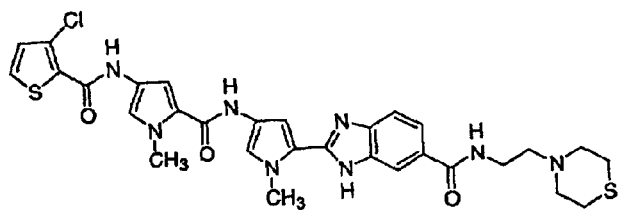
Figure 1G:
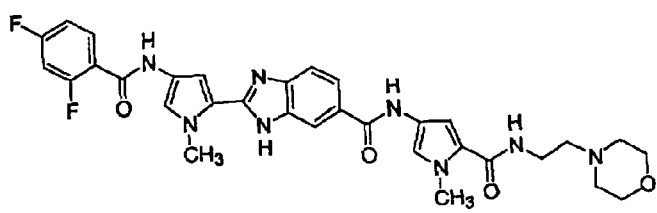
Figure 1G:
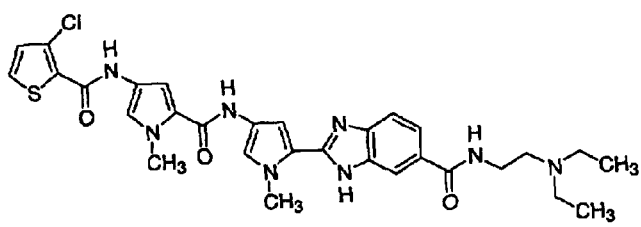

FIGS. 1a through 1g illustrate compounds according to this invention.

DETAILED DESCRIPTION OF THE INVENTION

Abbreviations and Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having six or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$–$C_4$)alkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl, heteroalkyl, aryl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R"and R'" each independently refer to hydrogen, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R',—NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —$N_3$, —CH(Ph)$_2$, perfluoro($C_1$–$C_4$)alkoxy, and perfluoro($C_1$–$C_4$)alkyl, in a number ranging from zero to the total number of open valences on the aromatic ring system; and where R', R"and R'" are independently selected from hydrogen, ($C_1$–$C_8$)alkyl and heteroalkyl, unsubstituted aryl and heteroaryl, (unsubstituted aryl)-($C_1$–$C_4$)alkyl, and (unsubstituted aryl)oxy-($C_1$–$C_4$)alkyl.

Two of the substituents on adjacent atoms of the aryl or heteroaryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$–$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, ascorbic, propionic, isobutyric, maleic, malonic, lactic, malic, glutamic, benzoic, succinic, suberic, fumaric, mandelic, phthalic, benzenesulfonic, p-tolylsulfonic, citric, tartaric, methanesulfonic, lactobionic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (chiral centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

In the discussions below, reference is made to dsDNA as the nucleic acid, but it is to be understood that the invention is not limited to dsDNA and is applicable to other nucleic acids, i.e., ribonucleic acid.

Compounds

Compounds (I) of this invention are polyamides (or oligoamides) having at least one aryl-benzimidazole (Ar-BIM) carboxamide unit and, optionally, aliphatic, aromatic, and/or heteroaromatic carboxamide units. Where m is 1, an Ar-BIM unit is positioned at one terminus (the N- or amino terminus), although additional Ar-BIM units may be present internally. Where m is 0, then all Ar-BIM units are positioned internally or at the C- or carboxy terminus. The number of carboxamide residues. (i.e., the degree of polymerization or oligomerization) is equal n+1 and is at least 2 if m is 1 (n is at least 1) and at least 3 if m is 0 (n is at least 2). n is preferably an integer from 3 to 12, inclusive, more preferably from 4 to 9, inclusive.

Compounds (I) are DNA-binding compounds, which bind to the minor groove of dsDNA. Different polyamide-dsDNA binding modes are possible. In the simplest mode, often referred to as the 1:1 binding mode, a single polyamide molecule fits in the channel formed by the minor groove. In what is referred to as the 2:1 binding mode, two polyamide molecules fit side-by-side in the minor groove, preferably aligned in an antiparallel manner (i.e., with one polyamide being aligned N-to-C and the other polyamide being aligned C-to-N, where "C" and "N" refer to the carboxy and amino termini, respectively of the polyamides). Lastly, in what is referred to as a "hairpin" binding mode, a single polyamide molecule that has a more or less centrally positioned flexible moiety (i.e., a moiety $M^3$, as discussed in greater detail hereinbelow) folds around itself to adopt a hairpin conformation when it is bound to the minor groove, so that a first portion of the polyamide at one side of the hairpin turn is adjacent to a second portion of the polyamide at the other side of the hairpin turn.

In formula (I)

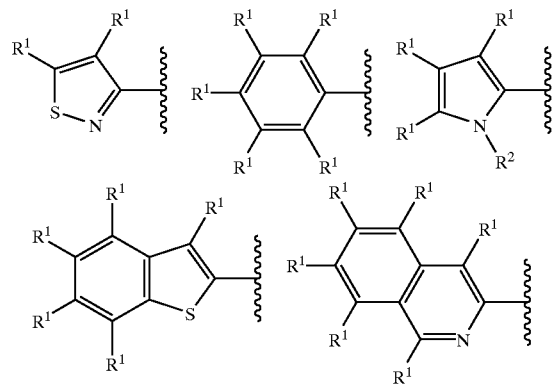

$Ar^1$ preferably is selected from the group consisting of

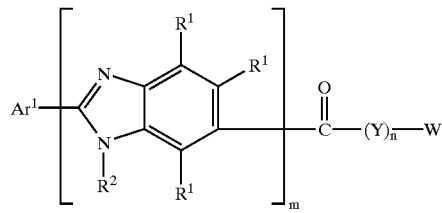

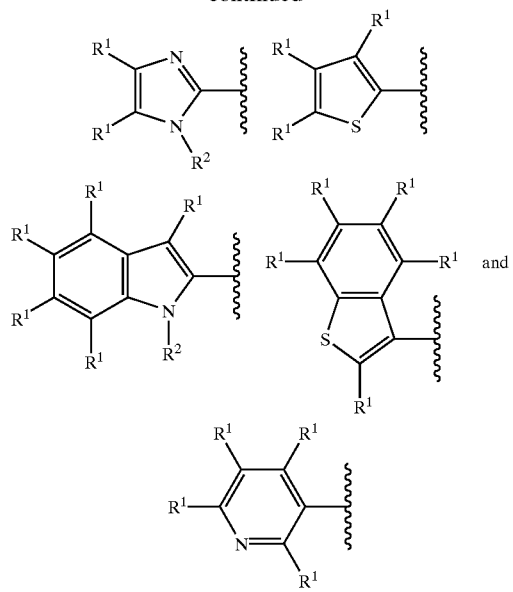

where $R^1$ and $R^2$ are as previously defined.

A more preferred $Ar^1$ is

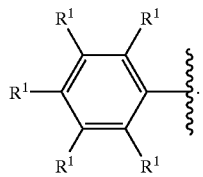

wherein at least one $R^1$ is halogen, more preferably F, Cl, or Br. One of the other $R^1$ groups may contain a basic group or a quaternized nitrogen, as defined hereinbelow. Specific examples include:

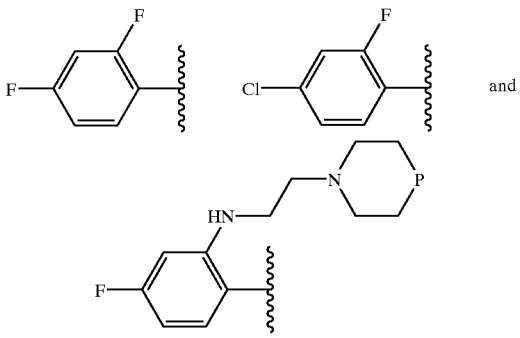

where P is O, S, or $CH_2$.

Another more preferred $Ar^1$ is

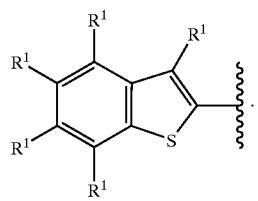

where $R^1$ is as previously defined. More preferably, the $R^1$ in the thienyl ring is Cl, as in

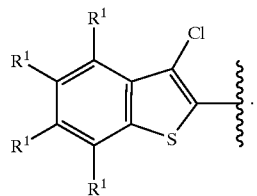

Yet another more preferred $Ar^1$ is

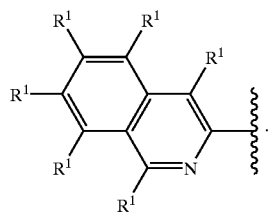

where $R^1$ is as previously defined. Even more preferably, all the $R^1$'s are H, as in

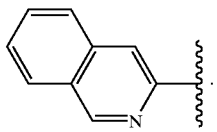

Yet another more preferred $Ar^1$ is

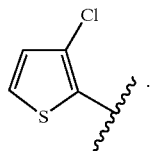

Moieties $M^1$, described by formulae IIa and IIb

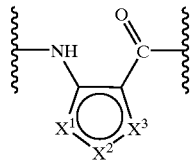

(IIa)

or

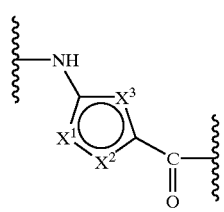

(IIb)

provide additional heteroaromatic polyamide building blocks. Moieties $M^1$ are 5-membered ring heteroaromatic moieties, the selection of $X^1$, $X^2$, and $X^3$ determining the type of heteroaromatic ring. Exemplary heteroaromatic rings include imidazole, pyrrole, pyrazole, furan, isothiazole, oxazole, isoxazole, thiazole, furazan, 1,2,3-thiadiazole, 1,2,4-thiadiazole, 1,2,5-thiadiazole, 1,3,4-thiadiazole, 1,2,3-triazole, 1,2,4-triazole, 1,3,4-oxadiazole, 1,2,4-oxadiazole, and thiophene. Preferably, at least one moiety Y is a moiety $M^1$.

The circle in the five-membered rings of formulae IIa and IIb above is meant to indicate the presence of two double bonds, which, in some embodiments, can move within the ring.

Preferred moieties $M^1$ are IIc (hereinafter "Py"), formally derived from 1-methyl-4-aminopyrrole-2-carboxylic acid, IId (hereinafter "Hp"), formally derived from 1-methyl-3-hydroxy-4-aminopyrrole-2-carboxylic acid, and IIe (hereinafter "Im"), formally derived from 1-methyl-4-aminoimidazole-2 carboxylic acid:

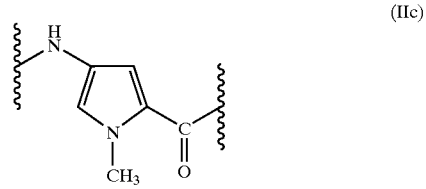

(IIc)

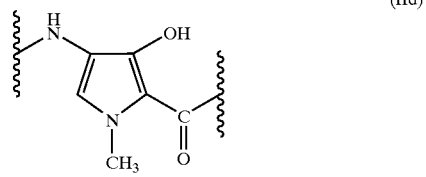

(IId)

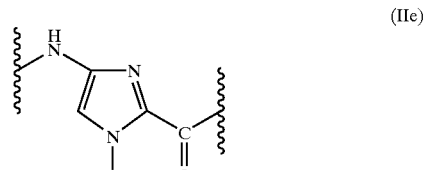

(IIe)

It has been shown by Dervan and co-workers (see, e.g., Dervan et al., U.S. Pat. No. 5,998,140 (1999); Dervan et al., WO 00/15209 (2000); Dervan, WO 00/15773 (2000); and Gottesfeld et al., WO 98/35702 (1998)) that, in a 2:1 binding mode to dsDNA, moieties Py, Im, and Hp moieties can be used to recognize specific dsDNA base pairs, giving rise to a set of "pairing rules" correlating heteroaromatic moiety pairs and DNA base pairs. These pairing rules are summarized below:

| Heteroaromatic Pair | dsDNA Base Pair(s) Recognized |
| --- | --- |
| Im/Py | G/C |
| Py/Im | C/G |
| Py/Py | A/T, T/A (degenerate) |
| Hp/Py | T/A |
| Py/Hp | A/T |

Such recognition can lead to sequence-specific dsDNA binding, enabling the design of compounds (I) that target predetermined DNA base pair sequences, for example, a specific promoter site or a sequence characteristic of a gene.

Optionally, compound (I) can include one or more moieties $M^2$

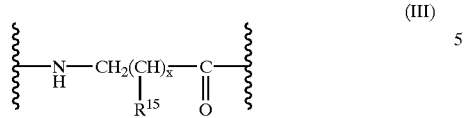
(III)

A moiety $M^2$ can function as a "spacer" for adjusting the positioning of the heteroaromatic moieties $M^1$ or $M^4$ relative to the dsDNA base pairs at the binding site. As a compound (I) binds in the minor groove, the alignment of heteroaromatic moieties $M^1$ and $M^4$ with the DNA base pairs with which they to interact of optimal binding or sequence recognition may drift as the number of heteroaromatic moieties $M^1$ and $M^4$ increases. Alternatively, incorporation of a moiety $M^2$ adds flexibility to compound (I), allowing its curvature to more accurately match that of the minor groove. The incorporation of one or more flexible moieties $M^2$ relaxes the curvature of the compound backbone, permitting larger compounds (I) to bind to longer sequences of DNA. In some preferred embodiments a moiety $M^2$ is present for every 4 to 5 heteroaromatic moieties $M^1$ or $M^4$, more preferably interrupting long sequences of $M^1$ and/or $M^4$ groups.

Preferred moieties $M^2$ are those corresponding to glycine (x=0 in formula III, depicted as IIIa below) and β-alanine (n=1 and $R^{15}$=H in formula III; depicted as IIIb below, hereinafter "β"), with the latter being especially preferred.

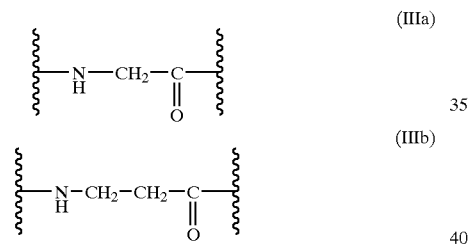
(IIIa)

(IIIb)

Moieties $M^2$ in which x=1 and $R^{15}$=OH, $NH_2$, or F can be used to alter the binding affinity and specificity (relative to β-alanine), as disclosed in Floreancig et al., *J. Am. Chem. Soc.*, 2000, 122, 6342; the disclosure of which is incorporated herein by reference.

When present in compound (I), optional moieties $M^3$ (formula IV)

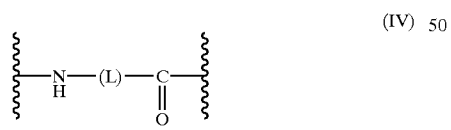
(IV)

have a group L providing a spacer of 3 to 4 atoms between —NH— and —C(=O)— and can be used to introduce a hairpin turn into compound (I). Exemplary moieties $M^3$ include:

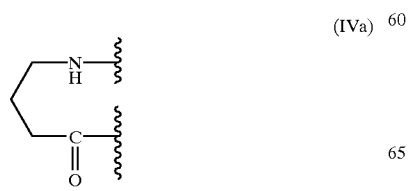
(IVa)

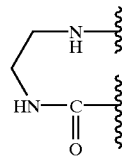
(IVb)

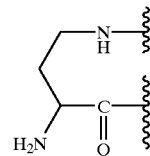
(IVc)

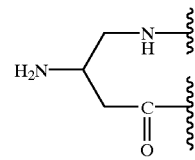
(IVd)

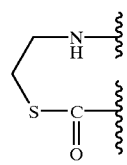
(IVe)

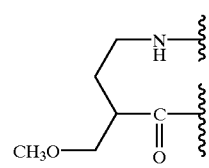
(IVf)

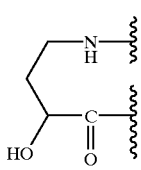
(IVg)

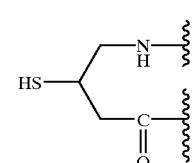
(IVh)

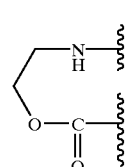
(IVi)

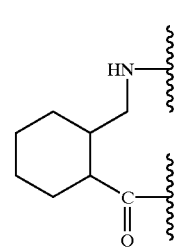
(IVj)

Moieties M⁴ (formula V) provide an additional and/or alternative source of Ar-BIM units in compound (I).

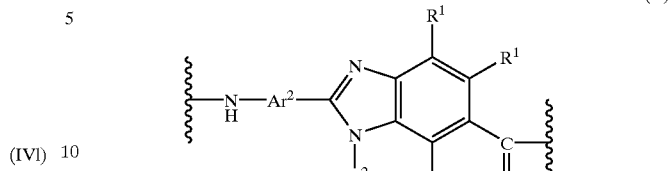
(V)

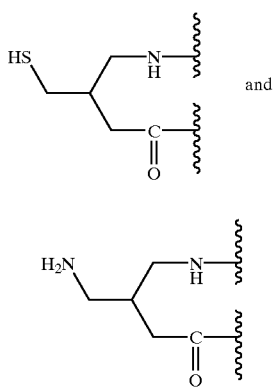
(IVk)
(IVl)

Moieties IVa (hereinafter "γ"), corresponding to γ-aminobutyric acid, and IVc, corresponding to 2,4-diaminobutyric acid, are preferred. Selecting one enantiomer or the other of moieties $M^3$ that are chiral allows stereochemical control of the binding of polyamides to the minor groove, for example as disclosed in Baird et al., WO 98/45284 (1998) in respect of R-2,4-diaminobutyric acid and S-2,4-diaminobutyric acid (corresponding to R-IVc and S-IVc, respectively).

Yet another class of moieties $M^3$ is represented by the formula

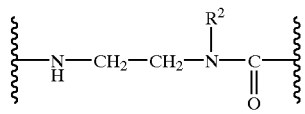

where $R^2$ is as previously defined.

While the group L preferably provides a 3-atom separation between the —NH— and the —(C=O)—, a 4-atom separation is also permissible, as illustrated by a 5-aminovaleric acid residue (i.e., L equals —(CH₂)₄—):

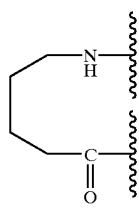

L can have pendant groups, which serve to enhance solubility or function as attachment points for other groups (e.g., IVc, IVd, IVg, IVh, IVk, IVl). The 3 to 4 atoms can be part of a larger group, which provides conformational rigidity (e.g., IVj). The 3 to 4 atoms can comprise carbon atoms only or it can include heteroatoms (e.g., IVb, IVe, IVi).

One or more moieties $M^4$ may be present, independent of whether m is 0 or 1. Among the $Ar^2$ moieties, preferred ones are thiophene (particularly halogen-substituted), pyrrole (particularly N-methylpyrrole), benzothiophene (particularly 3-halo substituted), imidazole (particularly N-methylimidazole), and isothiazole (particularly halogen substituted).

The group W can be viewed as a terminal group, located at the C-terminus of compound (I), forming an "amide cap" in the event W is $N(R^2)_2$ and an "ester" cap there in the event W is $OR^1$.

Preferably, W is $N(R^2)_2$. In such instance, the two groups $R^2$ can be linked to each other to form a cyclic structure. A group $N(R^2)_2$ can contain a basic group (as defined hereinbelow). Examples of groups $N(R^2)_2$ containing a basic group include:

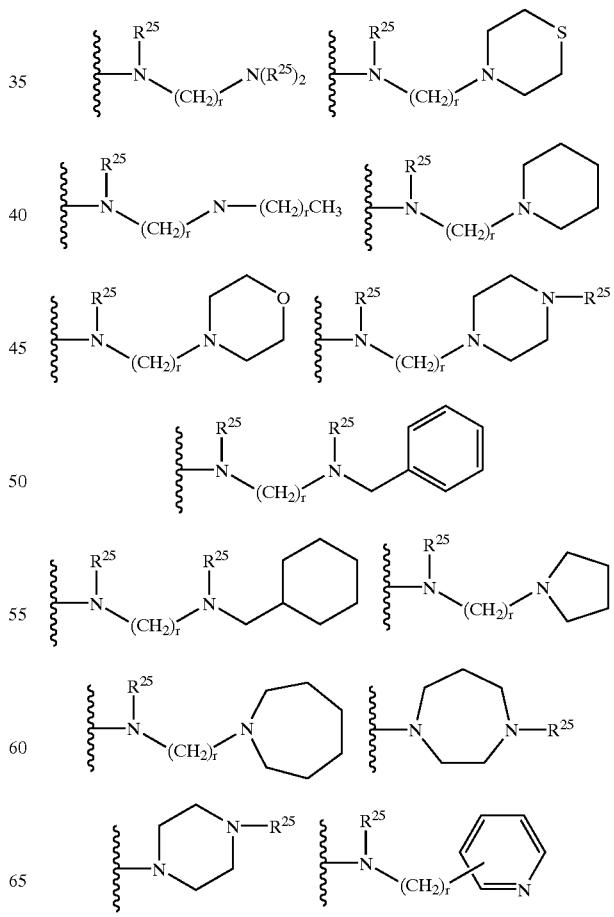

-continued

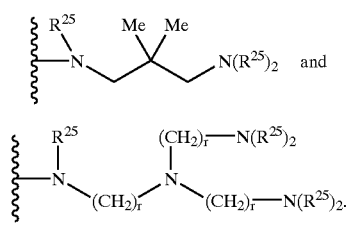

Examples of suitable groups $N(R^2)_2$ not containing a basic group include:

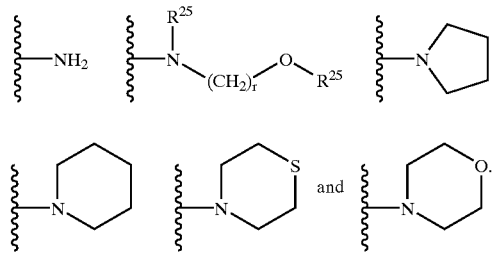

In the foregoing formulae, r is an integer ranging from 2 to 8, inclusive (preferably 2 to 6), and each $R^{25}$ is independently H, $CH_3$, $CH_2CH_3$, $CH_2CH_2CH_3$, or $CH(CH_3)_2$.

As used herein with reference to groups $R^1$ and $R^2$, "substituted or unsubstituted ($C_1$–$C_{12}$)alkyl group, or a substituted or unsubstituted ($C_1$–$C_{12}$)heteroalkyl group" includes not only conventional alkyl or cycloalkyl groups such as methyl, ethyl, propyl, isopropyl, butyl, s-butyl, isobutyl, t-butyl, cyclopentyl, cyclohexyl, and pentyl, but also unsaturated $C_1$ to $C_{12}$ groups, having for example aromatic, alkenyl, or alkynyl groups (e.g., phenyl, benzyl, vinyl, cyclohexenyl, etc.). One or more backbone carbons can be replaced by heteroatoms. There may be present functionalities such as hydroxy; oxo (=O); primary, secondary, or tertiary amine (e.g., —$NH_2$, —$NH(CH_3)$, —$N(CH_3)_2$); quaternary ammonium (e.g.,—$N(CH_3)_3^+$); alkoxy (e.g., methoxy, ethoxy); acyl (e.g., —C(=O)$CH_3$); amide (e.g., —NHC(=O)$CH_3$); thiol; thioether (e.g., —$SCH_3$); sulfoxide; sulfonamide (e.g., —$SO_2NHCH_3$); halogen (e.g., F, Cl); nitro; and the like. Exemplary specific $R^1$, $R^2$, $R^3$, $R^{10}$ $R^{11}$, and $R^{20}$ groups include methyl, trifluoromethyl, ethyl, acetyl, methoxy, methoxyethyl, ethoxyethyl, aminoethyl, hydroxyethyl, propyl, hydroxypropyl, cyclopropyl, isopropyl, 3-(dimethylamino) propyl, butyl, s-butyl, isobutyl, t-butyl, pentyl, cyclopentyl, vinyl, allyl, ethynyl, propynyl, and the like.

Compound (I) preferably has a basic group having a $pK_b$ of 12 or less or a quaternized nitrogen group. (Or, stated conversely, the conjugate acid of the basic group has a $pK_a$ greater than 2 ($pK_a$=14–$pK_b$).) Preferably, the $pK_b$ is less than 10, more preferably less than 5. A $pK_b$ of less than 12 ensures that compound (I) is protonated under the conditions in which it interacts with a nucleic acid. Preferably the basic group is a nitrogenous group, for example an amine, an amidine, a guanidine, a pyridine, a pyridazine, a pyrazine, a pyrimidine, an imidazole, or an aniline. Primary, secondary, or tertiary aliphatic amines, are preferred. Exemplary quaternized nitrogen groups include alkyl pyridinium and tetraalkyl ammonium groups such as:

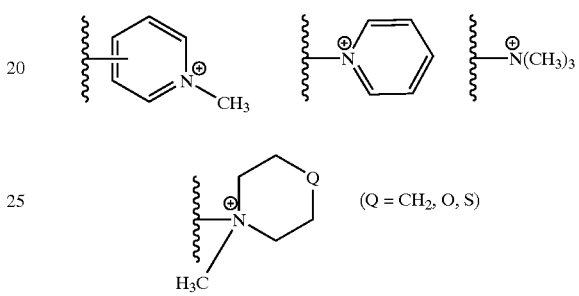

Without being bound by theory, it is believed that the basic group enhances cell transport properties, enabling the compounds of this invention to be transported across cellular and nuclear membranes and to reach dsDNA in the nucleus. See Rothbard et al., WO 98/52614 (1998), which discloses that guanidine or amidino side chain moieties enhance transport across biological membranes. Another possible benefit is enhancement of the binding affinity to the nucleic acid, perhaps via ionic interactions with backbone phosphate groups. See Baird and Dervan, WO 98/37087 (1998) and Bruice et al., U.S. Pat. No. 5,698,674 (1997). Lastly, the protonated basic group enhances the solubility of compounds (I).

Preferably, the basic group is present within the C-terminal group $N(R^2)_2$, but it may be present elsewhere in the molecule, for example as part of a group $R^1$ or $R^2$ in $M^1$, $M^4$, or $Ar^1$. Or, multiple basic groups may be present, at different parts of compound (I).

In a preferred embodiment, compound (I) is according to formula Ia:

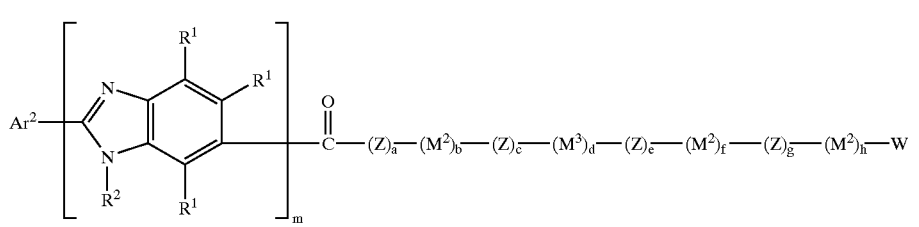

wherein $Ar^1$, $M^2$, $M^3$, $R^1$, $R^2$, and W have the same meanings as previously assigned; each Z is independently $M^1$ or $M^4$; each of a, c, e, g and h is an integer independently from 0 to 5, inclusive; and each of b, d, and f is independently 0 or 1. The sum of a, c, e, and g is at least 3.

In another preferred embodiment, compound (I) is according to formula Ib:

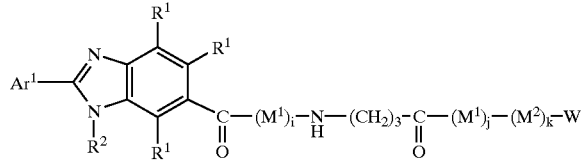

(Ib)

wherein $Ar^1$, $M^1$, $M^2$, $R^1$, $R^2$, and W are as previously defined; each of i and j is independently an integer from 1 to 5, inclusive, and k is an integer from 0 to 3, inclusive.

In yet another preferred embodiment, compound (I) is according to formula Ic:

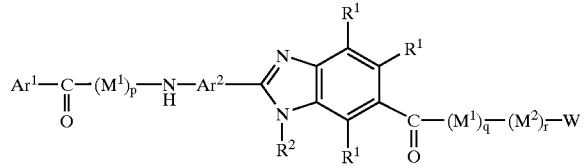

(Ic)

wherein $Ar^1$, $Ar^2$, $M^1$, $M^2$, $R^1$, $R^2$, and W are as previously defined; each of p and q is independently an integer from 1 to 5, inclusive, and r is an integer from 0 to 3, inclusive.

In yet another preferred embodiment, compound (I) is according to formula Id:

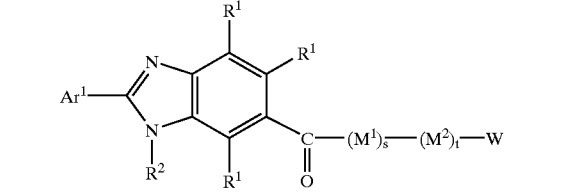

(Id)

wherein $Ar^1$, $M^1$, $M^2$, $R^1$, $R^2$, and W are as previously defined; s is an integer from 1 to 5, inclusive; and t is an integer from 1 to 3, inclusive.

In yet another preferred embodiment, compound (I) is according to formula Ie:

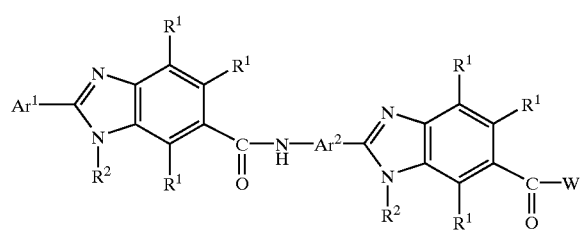

(Ie)

wherein $Ar^1$, $Ar^2$, $R^1$, $R^2$, and W are as previously defined.

In yet another preferred embodiment, compound (I) is according to formula If:

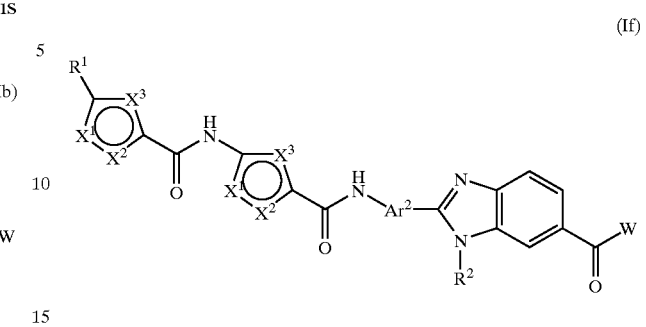

(If)

wherein $Ar^2$, $X^1$, $X^2$, $X^3$, $R^1$, $R^2$, and W are as previously defined. A more preferred variant of formula If has the structure:

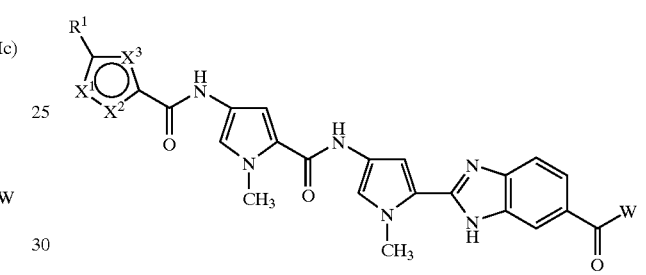

In yet another preferred embodiment, compound (I) is according to formula (Ig):

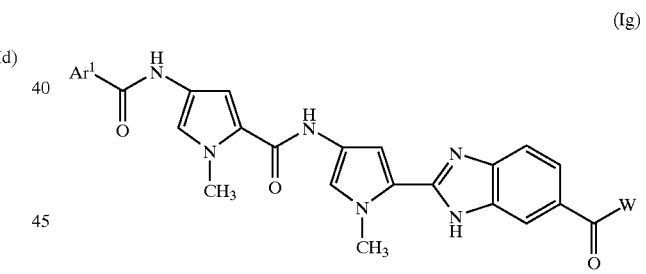

(Ig)

wherein $Ar^1$ and W are as previously defined.

In yet another preferred embodiment, compound (I) is according to formula (Ih):

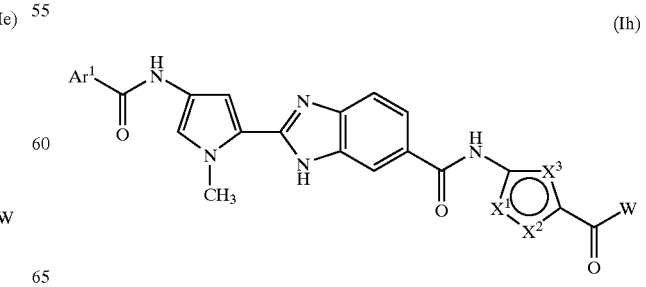

(Ih)

where $Ar^1$, $X^1$, $X^2$, $X^3$, and W are as previously defined. In formulae (Ig) and (Ih), $Ar^1$ preferably is

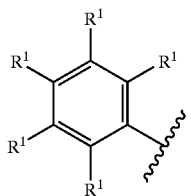

where $R^1$ is as previously defined except that at least one $R^1$ is halogen, preferably Cl or F;

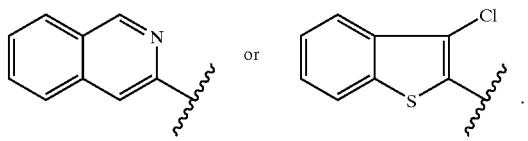

Also preferably in formulae (Ig) and (Ih), W is $N(R^2)_2$. An $R^2$ moiety may have a basic group having a $pK_b$ of 12 or less or a quaternized nitrogen group.

In compounds of formula (Ih), the moiety

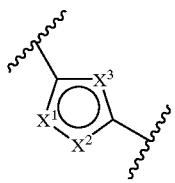

preferably is selected from the group consisting of

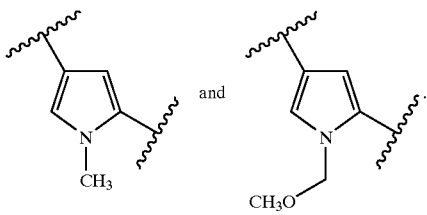

Compounds (Ia), (Ib), (Ic), (Id), (Ie), (If), (Ig), and (Ih), each may have a basic group having a $pK_b$ of 12 or less or a quaternized nitrogen group.

Illustrative specific compounds (I) are shown in FIGS. 1a through 1g. In the figures, the shorthand notations Py, Im, β, and γ have the meanings previously assigned.

Compounds (I) can be conjugated or linked to another nucleic acid binding compound. The conjugated nucleic acid binding compounds can be two identical or different compounds (I), or one compound (I) and a different class of nucleic acid binder, for example an intercalator, a triple helix former, a binder to the phosphate backbone, a major groove binder, another type of minor groove binder, and the like. A preferred site for forming the conjugating link is an amino, hydroxy, or thiol functionality in a group L in moiety $M^2$, which can be acylated or alkylated. The preparation of tandem linked nucleic acid binding polyamides in this manner is disclosed in Baird et al., WO 98/45284 (1998), the disclosure of which is incorporated herein by reference.

Compounds (I) also can be conjugated to other moieties, such as, peptides, proteins, transport agents, fluorophores or other reporter groups, and the like.

Compounds (I) preferably bind to dsDNA with high affinity, meaning an equilibrium association constant of at least $10^3$ $M^{-1}$, more preferably at least $10^6$ $M^{-1}$, and most preferably at least $10^9$ $M^{-1}$. The measurement of binding affinities by quantitative DNase I footprinting is disclosed in Dervan, WO 98/50582 (1998), and Trauger et al., Nature 382, 559 (Aug. 8, 1996); the disclosures of which are incorporated herein by reference.

Compounds of this invention can be used to form complexes with dsDNA, for the purpose of recognizing and/or isolating dsDNA strands containing particular base-pair sequences, for example for analytical or diagnostic purposes. Thus, in another aspect of this invention there is provided a complex between dsDNA and compound of this invention. In cellular systems or in living organisms, they can modulate the expression of a gene by binding to the gene or a promoter or repressor region thereof. Such modulation may be useful for therapeutic or research purposes.

Additionally, compounds of this invention have been found to have anti-bacterial properties and therefore may be used for combating (i.e., preventing and/or treating) infections in eukaryotic organisms. Other pathogens against which compounds of this invention can be useful include protozoa and viruses. For human anti-infective applications, an effective amount of a compound of this invention is used, optionally in combination with a pharmaceutically acceptable carrier. The composition may be dry, or it may be a solution. Treatment may be reactive, for combating an existing infection, or prophylactic, for preventing infection in an organism susceptible to infection. Preferably, compounds of this invention are used to treat infections by drug-resistant strains of bacteria, for example MRSA (methycillin resistant S. aureus), MRSE (methycillin resistant S. epidermis), PRSP (penicillin resistant S. pneumoniae) or VRE (vancomycin resistant Enterococci). By "drug-resistant" it is meant that the bacteria are resistant to treatment with conventional antibiotics.

Host organisms that can be treated include eukaryotic organisms, in particular plants and animals. The plant may be an agriculturally important crop, such as wheat, rice, corn, soybean, sorghum, and alfalfa. Animals of interest include mammals such as bovines, canines, equines, felines, ovines, porcines, and primates (including humans). Thusly, in another aspect of this inventions, there is provided a method for treating a bacterial infection—particularly an infection by Gram-positive bacteria—comprising administering to a patient in need of such treatment an effective amount of compound (I). Compounds of this invention can be used in the preparation of a medicament for treating a bacterial infection in a mammal. The compounds may be administered orally, topically, or parenterally (e.g., intravenously, subcutaneously, intraperitoneally, transdermally).

While not wishing to be bound by any particular theory, it is believed that the compounds of this invention derive their biological activity from their ability to bind to dsDNA.

Compounds I can be synthesized by solid phase techniques from the corresponding amino acids or their derivatives, for instance IIc', IId', and IIe' for the synthesis of the Py, Hp, and Im building blocks, respectively.

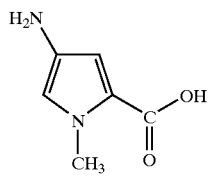
(IIc′)

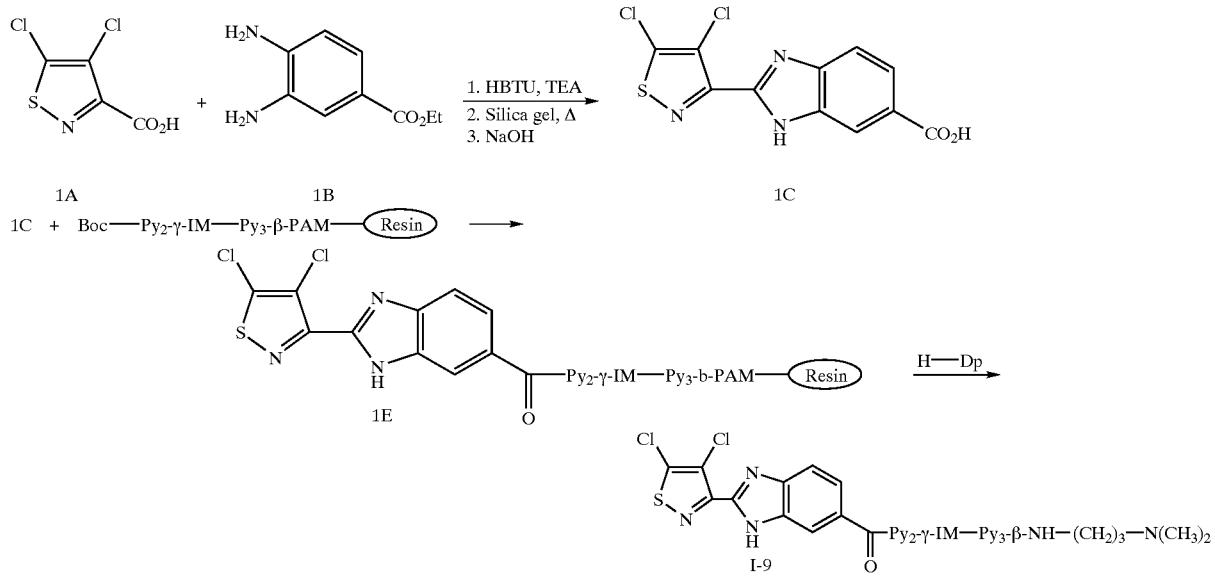

-continued

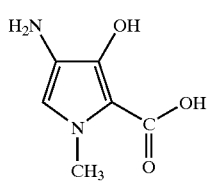
(IId′)

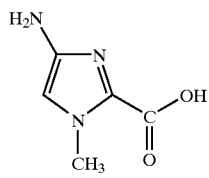
(IIe′)

In solid phase synthesis, a polyamide is synthesized on a resin such as Boc-glycine-PAM-resin or Boc-β-alanine-PAM-resin, with moieties Y being added in series of steps involving amino-protected and carboxy-activated monomers, as taught in Dervan et al., U.S. Pat. No. 6,090,947 (2000); Baird et al., WO 98/37066 (1998); Baird et al., WO 98/37067 (1998); and Dervan et al., WO 98/49142 (1998); the disclosures of which are incorporated herein by reference.

The practice of this invention may be further understood by reference to the following examples, which are provided by way of illustration and not of limitation.

Synthesis

Compound I-9

Compound I-9 was synthesized per Scheme 1, which illustrates a solid phase (resin supported) synthetic approach:

To a solution of 4,5-dichloroisothiazole-3-carboxylic acid (1A, 0.25 g, 1.3 mmol, commercially available) in N,N-dimethylformamide ("DMF," 5 mL) was added 2-(1H-benzotriazole-1-yl)-1,1,3,3-tetramethyluronium hexafluorophosphate ("HBTU," 0.45 g, 1.2 mmol) and triethylamine ("TEA," 0.71 mL, 5.0 mmol). The acid was activated for 10 minutes with stirring at room temperature. To the activated acid was added ethyl-3,4-diaminobenzoate (1B, 0.46 g, 2.6 mmol, commercially available). The reaction was stirred at room temperature overnight. Solvents were removed in vacuo and 0.182 g (40% yield) of the less polar monoamide product was isolated by column chromatography on silica gel (30% hexanes in ethyl acetate). The monoamide (0.050 g, 0.14 mmol) was dissolved in methylene chloride and absorbed onto silica gel and dried in vacuo. The silica gel was plated into a crystallizing dish and heated to 110° C. for 10 min. Thin layer chromatography of an eluted portion of the silica gel indicated complete reaction (cyclization to form benzimidazole ring system). The product was eluted from the silica (20% ethyl acetate in dichloromethane), and solvents were removed to yield 0.048 g (99% yield) of the ethyl ester of compound 1C. The product was taken up in 1 M NaOH and heated to 60° C. with stirring for 2 h. The reaction was cooled to 0° C. and neutralized with 1 M HCl. The precipitate formed was filtered and washed successively with water and dried to yield 0.037 g, 90% yield of carboxylic acid 1C. $^1$H NMR $\delta_H$ (DMSO-d$_6$) 8.23 (s, 1H), 7.91 (d, 1H, J=8.4 Hz), 7.64 (d, 1H, J=8.4 Hz). m/z (ES) 315.2 (MH$^+$).

Carboxylic acid 1C was activated and coupled to polyamide precursor 1D formed on solid phase support per published procedure (Baird, E. E.; Dervan, P. B., *J. Am. Chem. Soc.* 1996, 118, 6141; Dervan et al., U.S. Pat. No. 6,090,947 (2000)).

In precursor 1D, the partial formula

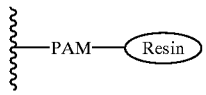

represents a solid phase support resin having attached thereto a phenylacetamidomethyl ("PAM") linkage group:

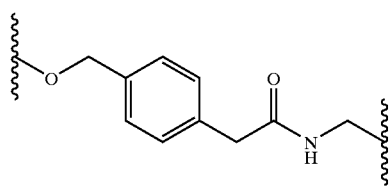

Precursor 1D preferably is made using commercially available Boc-β-alanine-PAM-resin, which has a Boc-protected β-alanyl residue attached to the resin via a PAM linkage:

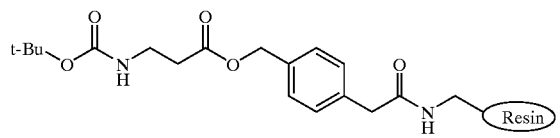

Boc-β-alanine-PAM resin

Cleavage of precursor 1E with N,N-dimethylaminopropylamine ("H-Dp") to yield compound I-9 and purification were performed per the published procedure with the exception that the cleavage step was carried out at room temperature. Purified fractions were characterized by electrospray mass spectrometry. Lyophilization yielded 10 mg of compound I-9.

Other compounds of this invention, such as I-4, I-5, I-6, and I-8 were analogously synthesized, replacing compound 1A with the commercially available 3-chlorothiophene-2-carboxylic acid, 3-chlorobenzothiophene-2-carboxylic acid, 4,5-dibromothiophene-2-carboxylic acid, or 1-methylimidazole-2-carboxylic acid, respectively, in the synthesis of the benzimidazole precursor, and with the exception that compounds I-4 and I-5 were synthesized in solution.

Synthesis of Compound I-3

The synthesis of compound I-3 is shown in Scheme 2, which illustrates a solution-phase synthetic approach:

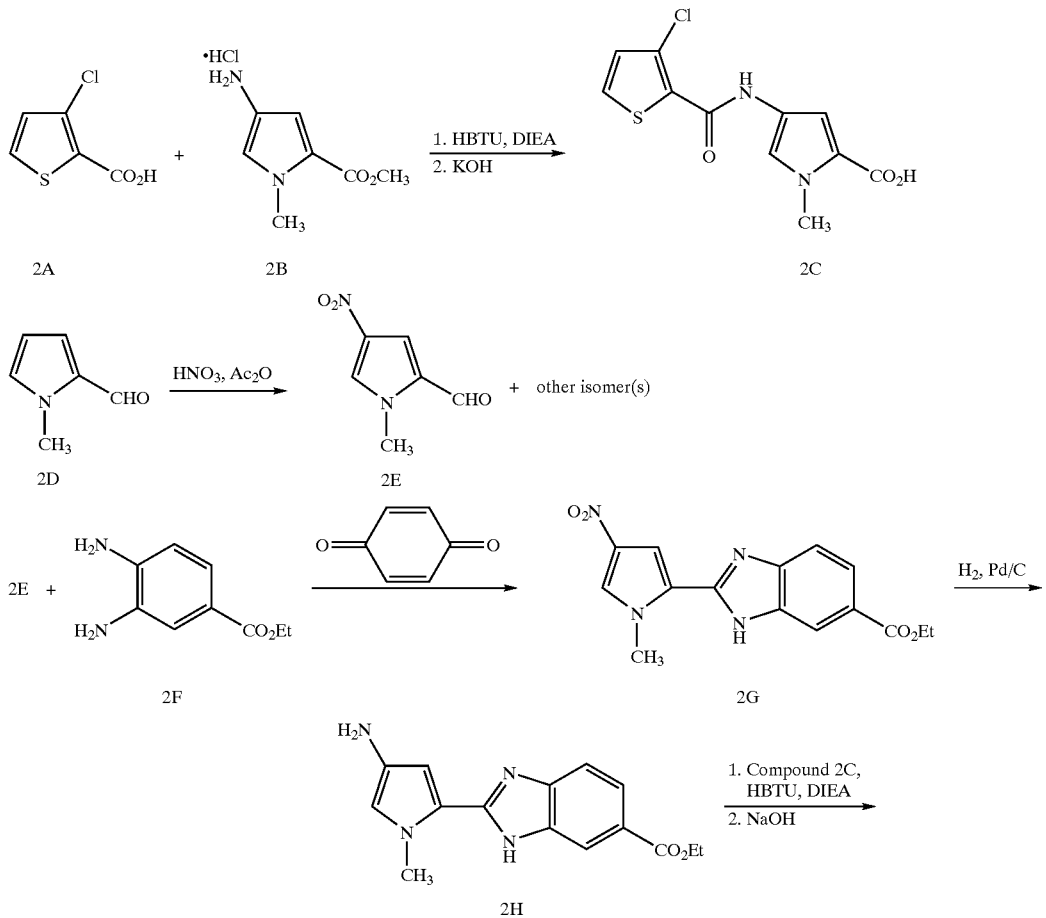

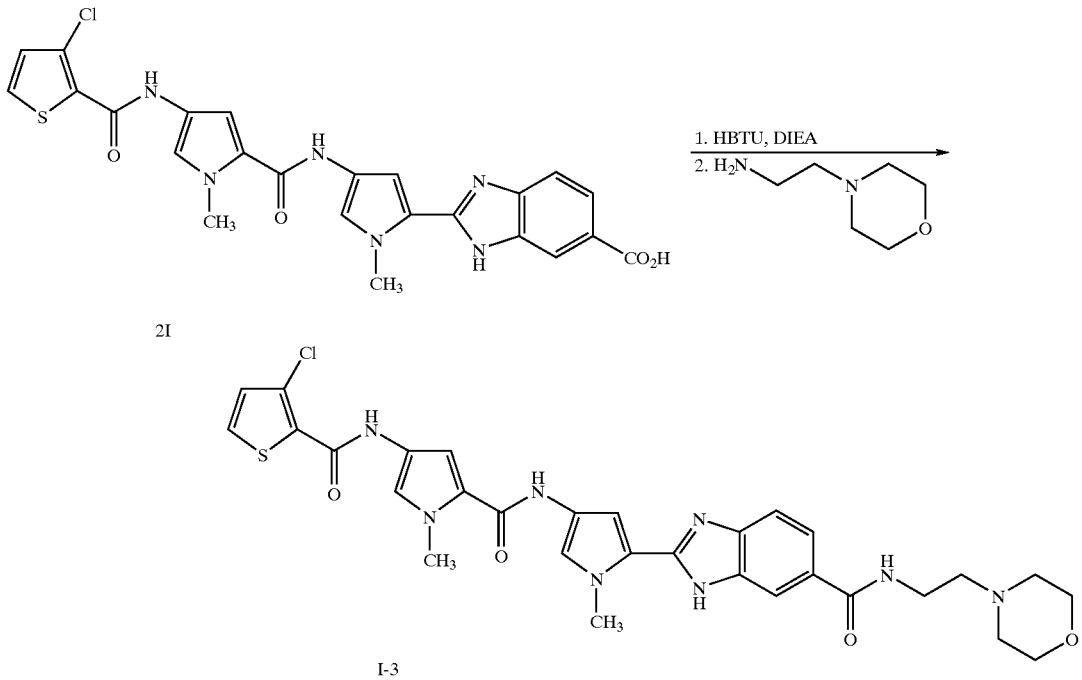

Synthesis of intermediate carboxylic acid 2C. To 3-chlorothiophene-2-carboxylic acid (2A, 5.31 g, 32.6 mmol, commercially available) in DMF (30 mL) was added HBTU (11.8 g, 31.1 mmol) and diisopropylethylamine ("DIEA," 6 mL). The reaction was stirred at room temperature for 30 min. To the solution was added methyl 4-amino-1-methylpyrrole-2-carboxylate hydrochloride (2B, 5.19 g, 27.2 mmol). The reaction was stirred at room temperature for 12 h. The reaction was poured dropwise into stirring ice water (800 mL). The precipitate was collected over a coarse frit, washed with hot water, and lyophilized to provide 9.1 g (112% yield) of crude methyl ester of compound 2C. To the methyl ester (8.1 g) was added water (50 mL), ethanol (50 mL), and KOH (5 g). The reaction was stirred at room temperature for 12 h. To the reaction was added water (500 mL). The solution was washed with ethyl acetate (1×100 mL). The aqueous layer was cooled to 0° C. and acidified to pH 2 with 7 M HCl. The resulting precipitate was filtered and washed successively with water, then dried in vacuo to provide near quantitative yield of the intermediate carboxylic acid 2C.

Nitration of N-methylpyrrole carboxaldehyde 2D. To acetic anhydride (240 mL) cooled at 0° C. was added fuming nitric acid (33.5 mL). After cooling, the mixture was added dropwise via addition funnel to a solution of N-methyl pyrrole carboxaldehyde (2D, 50 g, 458 mmol, commercially available) in acetic anhydride (240 mL) cooled to −40° C. in dry ice acetonitrile bath. Following addition of the nitration reagent and upon temperature stabilization, the reaction was allowed to slowly reach 10° C. At this point the temperature can increase rapidly. Between 10 and 20° C., the solution was immediately poured onto ice (480 g). The reaction was allowed to sit at room temperature overnight. Crystals formed. The solution was brought to 5° C. for 1 h, then filtered. The crystals formed were recrystalized from 100 mL of ethanol to provide 10.1 g of the desired isomer 2E. Further crystallization from ethanol provides an additional 7.64 g of desired isomer 2E.

Synthesis of benzimidazole intermediate 2H. A solution of 3-nitro pyrrole-5-carboxaldehyde (2E, 10 g, 64.9 mmol) and ethyl-3,4-diaminobenzoate (2F, 12.4 g, 69.1 mmol) in DMF (325 mL) was brought to 80° C. and stirred for 1 h. To the reaction was added benzoquinone (10.6 g, 97.6 mmol). The reaction was brought to 120° C. and stirred for 2 h. Solvent was removed in vacuo and 600 mL of dichloromethane were added to the solids. The suspension was boiled down to half volume, then stored at −25° C. for 1 h. Solids were filtered, rinsed with dichloromethane until filtrate ran clear. The solids were brought up in ethanolic HCl. Solvent was removed in vacuo. The product was crushed, precipitated from ethanol (600 mL), and filtered, and rinsed with cold ethanol (100 mL). Removal of ethanol from solids provided 17.49 g of the HCl salt of the nitro analog of compound 2H. To the HCl salt (0.37 g, 1.17 mmol) was added DMF (6 mL) and 10% Pd on carbon (0.3 g). The flask was fitted with a $H_2$ balloon and stirred overnight. The solution was filtered to provide compound 2H, which was used in subsequent steps without removal of the solvent.

Coupling of compounds 2C and 2H. In a separate flask, compound 2C (0.122 g, 0.43 mmol) was activated with HBTU (0.16 g, 0.41 mmol), DIEA (0.10 mL, 0.59 mmol), in DMF (1 mL). A solution of compound 2H representing a theoretical amount of 0.39 mmol was added to activated compound 2C. The reaction was shaken in a 37° C. incubator for 2 h. Solvents were removed in vacuo. The resulting crude ethyl ester of compound 2I was suspended in MeOH (3.2 mL) and 2 N NaOH (3.2 mL). The reaction was stirred at 60° C. overnight. MeOH was removed in vacuo. The basic solution was neutralized with 2 N HCl. The precipitated compound 2I was filtered and washed with water. Excess water was removed in vacuo.

Conversion to compound I-3. The resulting crude compound 2I (0.17 g, 0.32 mmol) was activated with HBTU (0.12 g, 0.32 mmol), DIEA (0.11 mL, 0.65 mmol), in DMF (1 mL). To the activated compound 2I was added N-aminoethylmorpholine (0.21 mL, 1.6 mmol). The solution was shaken at 37° C. for 2 h. Solvents were removed in vacuo. The final product was purified as before by reverse phase HPLC to yield 67 mg of compound I-3. $^1$H NMR $\delta_H$ (DMSO-d$_6$) 10.2 (s, 1H), 10.1 (s, 1H), 9.57 (s, 1H), 8.69 (s, 1H) 7.87 (d, 1H, J=5.6 Hz), 7.74 (d, 1H, J=8.0 Hz), 7.36 (s, 1H), 7.30 (s, 1H), 7.19 (d, 1H, J=5.2 Hz), 7.14 (s, 1H), 7.10 (s, 1H), 4.08 (s, 3H), 4.02 (m, 2H), 3.89 (s, 3H), 3.62 (m, 7 H), 3.18 (m, 4H).

m/z (ES) 636.1 (MH$^+$).

Compound I-7 was prepared by the same general method, replacing compound 2C with compound 1C, whose synthesis was described above, and also replacing N-aminoethylmorpholine with N,N-dimethylaminopropylamine in the last step. Compounds I-1 and I-2 were also analogously synthesized. Further, other building blocks may be coupled to compound 2H, for instance various halogenated benzoic acids or isoquinoline-3-carboxylic acids (or their derivatives), to prepare compounds such as I-22, I-28, I-35, and I-39. Or, building blocks of the type

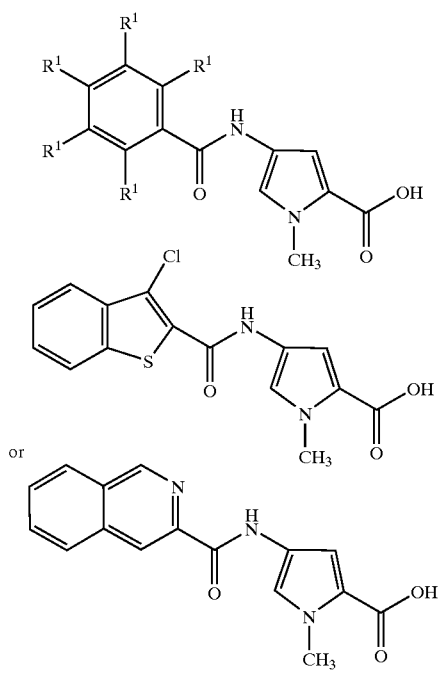

(or their derivatives) can be couple to compound 2H en route to compounds such as I-13 to I-21, I-23 to I-27, and the like.

Synthesis of Compounds Having Pendant Amine Groups

Compounds such as I-16 to I-18, in which the N-terminal phenyl group has a pendant amine substituent, are synthesized from the corresponding fluoro compound by nucleophilic aromatic substitution of the fluorine by the corresponding amine, using reaction conditions of 48 hr at 60–70° C. in NMP. For instance, the treatment of corresponding 2,4-difluoro compound with 4-(2-aminoethyl)morpholine under such conditions gave compound I-16 (selective substitution).

Synthesis of Methoxymethylated Building Block

Boc-protected, methoxymethylated aminopyrrole carboxylic acid

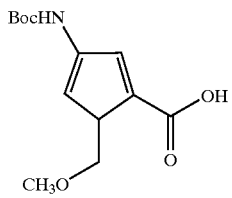

used in the synthesis of compounds such as I-34, was prepared by alkylation of ethyl 4-nitropyrrole-2-carboxylate with methoxymethyl chloride followed by hydrogenation (H$_2$, Pd) and Boc-protection (Boc$_2$O). The Boc-protected amino ester was saponified to give acid.

Those skilled in the art will appreciate that the synthetic techniques described hereinabove may be used to prepare other compounds according to this invention, replacing an intermediate or precursor compound with a different one.

Biological Activity

Compounds according to this invention were screened for their in vitro activities against selected species of bacteria and fungi. The minimal inhibition concentration (MIC) of these compounds was determined using the National Committee for Clinical Laboratory Standards (NCCLS) broth microdilution assay in microtiter plates, as set forth in: (1) the guidelines of the National Committee for Clinical Laboratory Standards (NCCLS) Document M7-A4 (NCCLS, 1997); (2) the guidelines of the National Committee for Clinical Laboratory Standards (NCCLS) Document M11-A4 (NCCLS, 1997); and (3) the guidelines and reference method of the National Committee for Clinical Laboratory Standards (NCCLS) Document M27-T (NCCLS, 1995). For antifungal essays, the method recommended in Murray, PR., 1995 *Manual of Clinical Microbiology* (ASM Press, Washington, D.C.), was employed. The results are presented in Table 1 below.

TABLE 1

| | Organism (Minimum Inhibitory Concentration (MIC), µg/mL) | | | | | | |
|---|---|---|---|---|---|---|---|
| Compound | A | B | C | D | E | F | G |
| I-1 | +++ | >32 | >32 | +++ | +++ | +++ | ND |
| I-2 | +++ | >32 | >32 | +++ | +++ | +++ | ND |
| I-3 | +++ | >32 | +++ | +++ | +++ | +++ | ND |
| I-4 | >32 | >32 | >32 | >32 | ND | +++ | + |
| I-5 | >32 | >32 | >32 | >32 | ND | >32 | >32 |
| I-6 | >32 | >32 | >32 | >32 | ND | >32 | >32 |

Key to organisms tested against:
A = *B. cereus* ATCC 11778
B = *C. albicans* ATCC 38247
C = *E. coli* ATCC 25922
D = *E. faecalis* ATCC 29212
E = *S. aureus* ATCC 13709
F = *S. pneumoniae* ATCC 49619
G = *S. aureus* ATCC 29213
Key to activity:
+++ = MIC ≤4
++ = MIC between 4 and 12
+ = MIC from 12 to 32, inclusive
ND = Not determined
>32 = preliminary data indicates MIC greater than 32

The above data shows that compounds (I) are active antimicrobial activity, especially against Gram-positive bacteria.

Further, compounds (I) are effective against drug-resistant bacteria, as evidenced by the data in Table 2 below:

TABLE 2

| | Organism (Minimum Inhibitoty Concentration (MIC), µg/mL) | | | | |
|---|---|---|---|---|---|
| Compound | A | B | C | D | E |
| I-1 | ND | +++ | ND | ND | ND |
| I-2 | +++ | +++ | +++ | +++ | +++ |

TABLE 2-continued

| Compound | Organism (Minimum Inhibitoty Concentration (MIC), µg/mL) | | | | |
|---|---|---|---|---|---|
|  | A | B | C | D | E |
| I-3 | +++ | +++ | ND | +++ | +++ |
| I-13 | +++ | +++ | +++ | +++ | +++ |
| I-14 | +++ | +++ | +++ | +++ | +++ |
| I-15 | +++ | +++ | +++ | +++ | +++ |
| I-16 | ND | + | ND | ND | ND |
| I-17 | ND | +++ | ND | ND | ND |
| I-18 | ND | +++ | ND | ND | ND |
| I-19 | +++ | +++ | +++ | +++ | +++ |
| I-20 | +++ | +++ | +++ | +++ | +++ |
| I-21 | +++ | +++ | +++ | +++ | +++ |
| I-22 | +++ | +++ | +++ | +++ | +++ |
| I-23 | +++ | +++ | ++ | +++ | +++ |
| I-24 | ND | +++ | ND | ND | ND |
| I-25 | ND | +++ | ND | ND | ND |
| I-26 | +++ | +++ | + | +++ | +++ |
| I-27 | +++ | +++ | ND | +++ | ND |
| I-28 | +++ | +++ | ND | +++ | ND |
| I-29 | +++ | +++ | +++ | +++ | +++ |
| I-30 | +++ | +++ | ND | +++ | ND |
| I-31 | +++ | +++ | +++ | +++ | +++ |
| I-32 | +++ | +++ | +++ | +++ | +++ |
| I-33 | +++ | +++ | +++ | +++ | +++ |
| I-34 | ND | ND | +++ | +++ | ND |
| I-35 | +++ | +++ | +++ | +++ | +++ |
| I-36 | +++ | +++ | +++ | +++ | +++ |
| I-37 | ND | +++ | +++ | ND | ND |
| I-38 | +++ | +++ | +++ | +++ | +++ |
| I-39 | +++ | +++ | +++ | +++ | +++ |
| I-40 | +++ | +++ | +++ | +++ | +++ |

Key to organisms tested against:
A = *E. faecium* ATCC 51559
B = *S. aureus* ATCC 27660
C = *S. aureus* ATCC 33591
D = *S. epidermis* ATCC 12228
E = *S. pneumoniae* ATCC 51422
Key to activity:
+++ = MIC ≦4
++ = MIC between 4 and 12
+ = MIC from 12 to 32, inclusive
ND = Not determined
>32 = preliminary data indicates MIC greater than 32

ATCC 27660 and ATCC 33591 are methycillin resistant strains of *S. aureus* (MRSA's). ATCC 51559 is a vancomycin resistant strain of *E. faecium* (VRE). ATCC 12228 is a methycillin resistant strain of *S. epidermis* (MRSE). ATCC 51422 is a penicillin resistant strain of *S. pneumoniae*. Compounds of this invention preferably have an MIC of 4 or less against at least one strain of drug resistant bacteria, such as the foregoing strains.

DNA Binding

A number of compounds according to this invention were screened for their ability to bind to three DNA sites, using DNase I footprinting. Generally, the procedure described in Dervan, WO 98/50582 (1998), was followed.

A plasmid was prepared by hybridizing two sets of 5'-phosphorylated complementary oligonucleotides, one set being

5'-CTAGATGCCGCTAAGTACTATGCCGCTAACTACTATGCCGCTAATTACTATGCCGC-3' and

5'-CATAGTAATTAGCGGCATAGTAGTTAGCGGCATAGTACTTAGCGGCAT-3' and the other set being

5'-TAAATACTATGCCGCTAACTAGTATGCCGCTATGCA-3' and

5'-TAGCGGCATACTAGTTAGCGGCATAGTATTTAGCCG-3'

The target sites and their complements are identified in bold underline.

The resulting duplexes were ligated to the large pUC19 XbaI/PstI restriction fragment. The 3'-P32 end-labeled EcoRI/PvuII fragment was prepared by digesting the plasmid with EcoRI and PvuII with simultaneous fill-in using Sequenase v. 2.0, [alpha-P32]-deoxyadenosine-5'-triphosphate, and [alpha-P32]-thymidine-5'-triphosphate, and isolating the cloned fragment by nondenaturing gel electrophoresis. A and G sequencing reactions were carried out as described. (Maxam and Gilbert, *Methods Enzymol.*, 1980, 65, 499–560; Iverson and Dervan, *Methods Enzymol.*, 1987, 15, 7823–7830; Sambrook et al., 1989, *Molecular Cloning*, 2nd ed., Cold Spring Harbor Laboratory Press: Cold Spring Harbor, N.Y.) Standard methods were used for all DNA manipulations. (Sambrook et al., ibid.)

Quantitative DNase I footprint titration experiments were carried out as described previously (Dervan, WO 98/50582, 1998) with the following changes. All reactions were carried out in a total volume of 400 µL, with polyamide stock solution or water added to 15000 cpm radiolabeled restriction fragment affording final solution conditions of 10 mM TrisHCl, 10 mM KCl, 10 mM $MgCl_2$, 5 mM $CaCl_2$, pH 7.0 and 0.01 nM, 0.1 nM, 1.0 nM, 10.0 nM polyamide or no polyamide for reference lanes. The polyamides were allowed to equilbrate at 22° C. for 16 h. Footprinting reactions were initiated with addition of 10 µL of a DNase I stock solution (at the appropriate concentration to give ~50% intact DNA) containing 1 mM DTT and allowed to proceed for 7 min at 22° C. The reactions were stopped, ethanol precipitated, resuspended in loading buffer, heat denatured, and placed on ice as described previously (Dervan, ibid.). The reaction products were separated on a precast 8% polyacrylamide denaturing sequencing Castaway gel with 32 preformed wells from Stratagene in 1×TBE at 2000 V. Gels were dried according to the manufacturer and exposed to a storage phosphor screen (Molecular Dynamics). Quantitation and data analysis were carried out as described in Dervan, ibid.

The results are presented in Table 3 below:

TABLE 3

| DNA Sequence | DNA Binding Compound (Association Constant, $K_a$, $M^{-1}$) | | | |
|---|---|---|---|---|
| | I-8 | I-9 | A | B |
| AGTACT | $1 \times 10^{11}$ | $1 \times 10^{11}$ | $3 \times 10^9$ | $1 \times 10^{11}$ |
| ACTACT | $5 \times 10^9$ | $5 \times 10^9$ | $5 \times 10^8$ | $7 \times 10^9$ |
| ATTACT | $5 \times 10^9$ | $5 \times 10^9$ | $5 \times 10^8$ | $7 \times 10^9$ |
| AATACT | $1 \times 10^9$ | $1 \times 10^9$ | $5 \times 10^5$ | $7 \times 10^9$ |
| ACTAGT | $<1 \times 10^8$ | $<1 \times 10^8$ | $<1 \times 10^8$ | $<1 \times 10^8$ |

Compounds A and B in Table B are comparison compounds without aryl-benzimidazole groups, having respectively the structures:

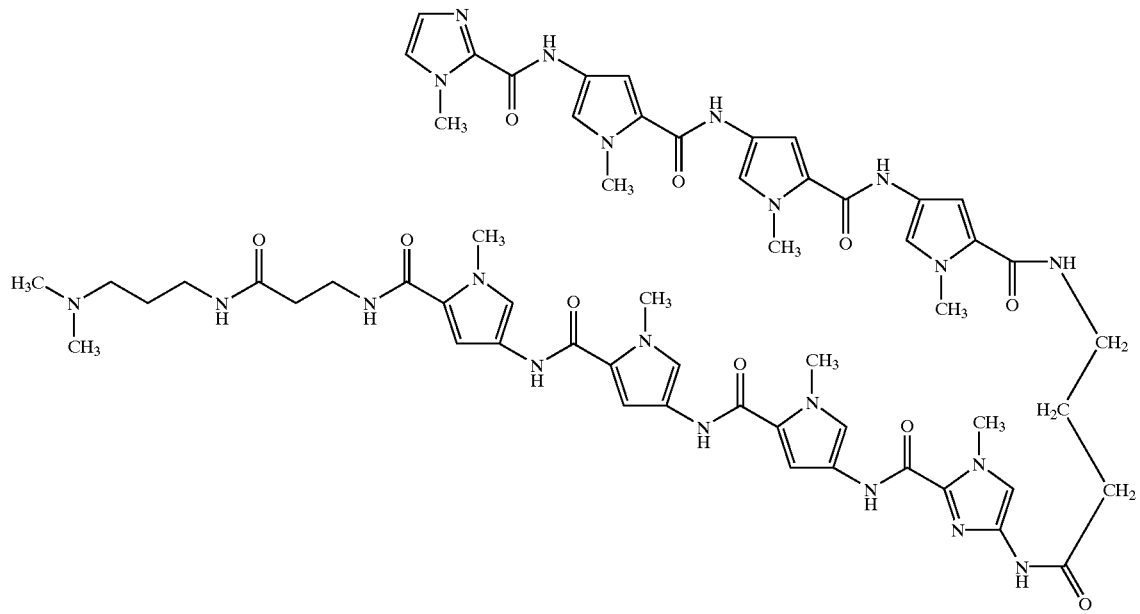

(A)

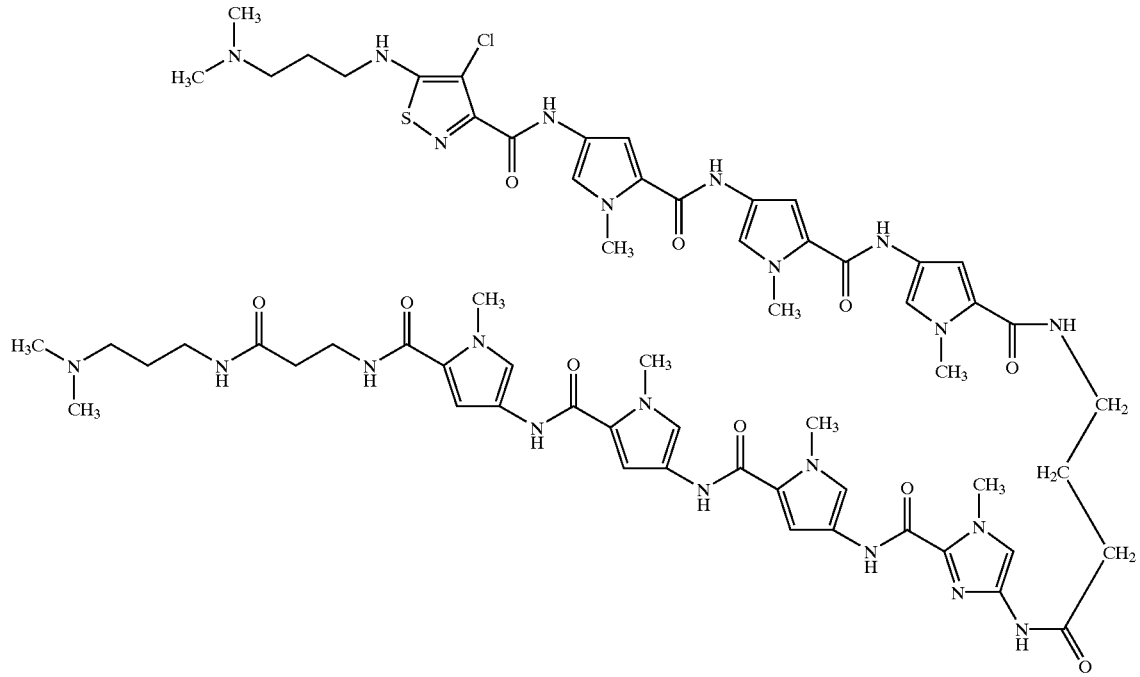

(B)

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. A compound having the formula

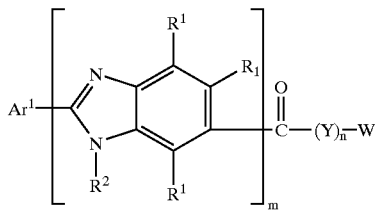

and pharmaceutically acceptable salts thereof, wherein
$Ar^1$ is a substituted or unsubstituted phenyl, naphthyl, 5-member heteroaromatic, 6-member heteroaromatic, or fused ring heteroaromatic group;
subscript m is 0 or 1 and subscript n is an integer from 1 to 25, inclusive, with the provisos that if m is 0, then at least one moiety Y is a moiety $M^4$ and n is at least 2;
each moiety Y is independently selected from the group consisting of
(a) moieties $M^1$ having the formula

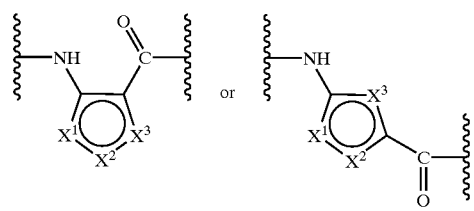

wherein
one of $X^1$, $X^2$, and $X^3$ is a ring vertex selected from the group consisting of —O—, —S—, and —$NR^2$—, and the other two of $X^1$, $X^2$, and $X^3$ are ring vertices selected from the group consisting of =N— and =$CR^1$—;
(b) moieties $M^2$ having the formula

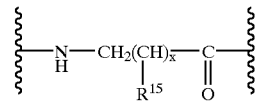

wherein
x is 0 or 1 and
each $R^{15}$ is independently H, OH, $NH_2$, or F;
(c) moieties $M^3$ having the formula

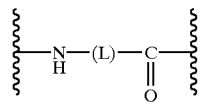

wherein each L is independently a divalent moiety separating —NH— and —(C=O)— by 3 or 4 atoms; and
(d) moieties $M^4$ having the formula

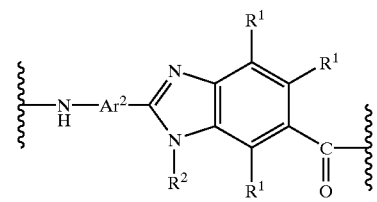

wherein each $Ar^2$ is independently selected from the group consisting of

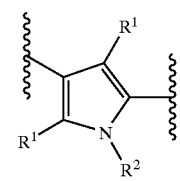 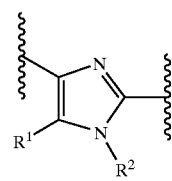

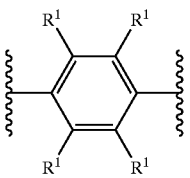 and 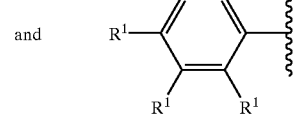

W is $N(R^2)_2$ or $OR^2$;
wherein in the preceding formulae
each $R^1$ is independently H, F, Cl, Br, I, CN, OH, $NO_2$, $NH_2$, a substituted or unsubstituted ($C_1$–$C_{12}$)alkyl group, or a substituted or unsubstituted ($C_1$–$C_{12}$) heteroalkyl group; and
each $R^2$ is independently H, a substituted or unsubstituted ($C_1$–$C_{12}$)alkyl group, or a substituted or unsubstituted ($C_1$–$C_{12}$)heteroalkyl group.

2. A compound according to claim 1, wherein $Ar^1$ is selected from the group consisting of:

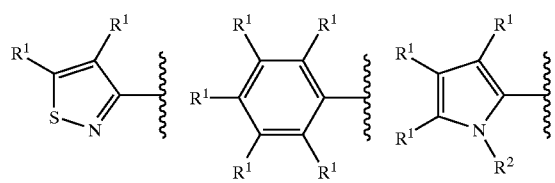

-continued

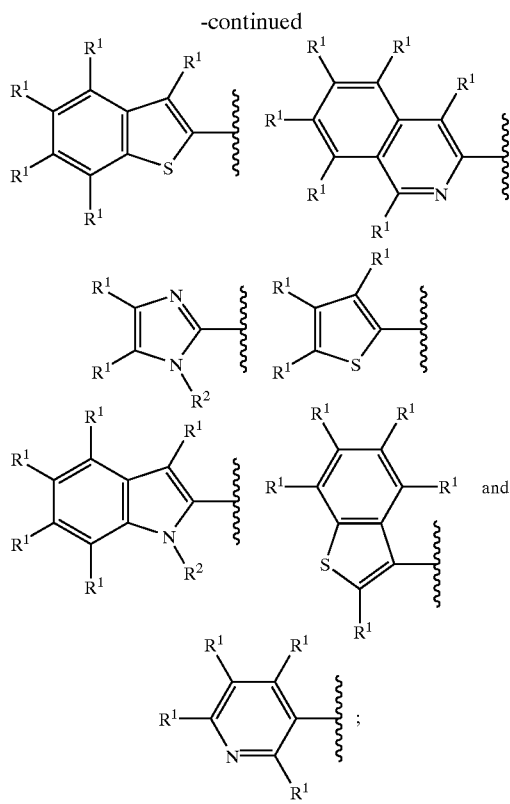

wherein $R^1$ and $R^2$ are as defined in claim 1.

3. A compound according to claim 2, wherein $Ar^1$ is

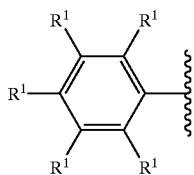

wherein at least one $R^1$ is halogen.

4. A compound according to claim 3, wherein an $R^1$ group in $Ar^1$ contains a basic group having a $pK_b$ of 12 or less or a quaternized nitrogen.

5. A compound according to claim 3, wherein $Ar^1$ is selected from the group consisting of

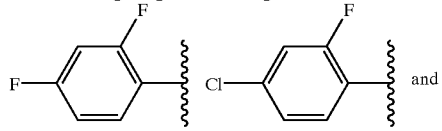

-continued

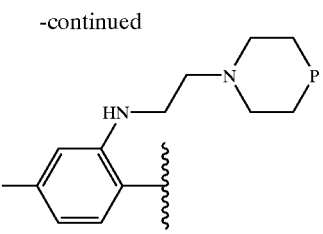

wherein P is O, S, or $CH_2$.

6. A compound according to claim 2, wherein $Ar^1$ is

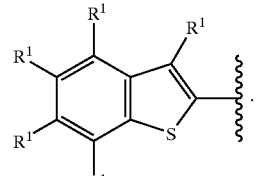

7. A compound according to claim 6, wherein $Ar^1$ is

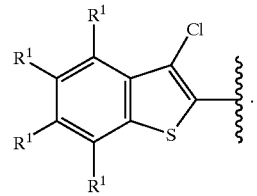

8. A compound according to claim 2, wherein $Ar^1$ is

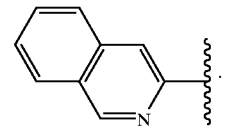

9. A compound according to claim 2, wherein $Ar^1$ is

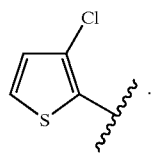

10. A compound according to claim 1, of the formula

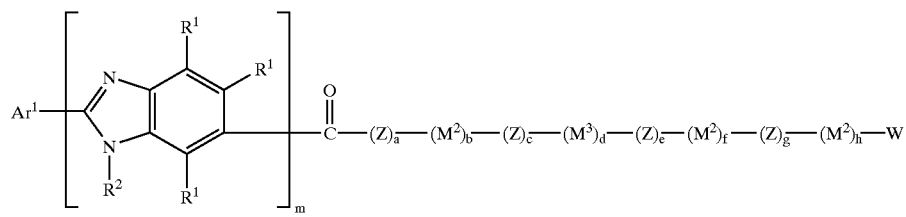

wherein Ar¹, M², M³, R¹, R², and W are as defined in claim 1; each Z is independently M¹ or M⁴; each of a, c, e, g and h is an integer independently ranging from 0 to 5, inclusive;

and each of b, d, and f is independently 0 or 1; with the proviso that the sum of a, c, e, and g is at least 3; said compound having a basic group having a $pK_b$ of 12 or less or a quaternized nitrogen group.

11. A compound according to claim 10, wherein W is $N(R^2)_2$.

12. A compound according to claim 1, of the formula

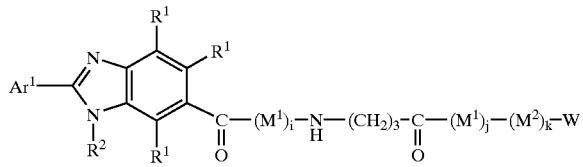

wherein Ar¹, M¹, M², R¹, R², and W are as defined in claim 1; each of i and j is independently an integer from 1 to 5, inclusive; and k is an integer from 0 to 3, inclusive; said compound having a basic group having a $pK_b$ of 12 or less or a quaternized nitrogen group.

13. A compound according to claim 12, wherein W is $N(R^2)_2$.

14. A compound according to claim 1, of the formula

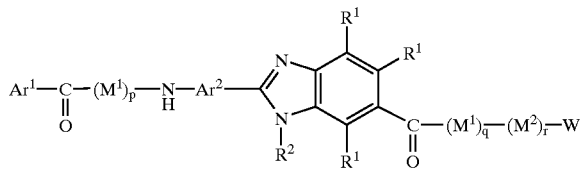

wherein Ar¹, Ar², M¹, M², R¹, R², and W are as defined in claim 1; each of p and q is independently an integer from 1 to 5, inclusive; and r is an integer from 0 to 3, inclusive; said compound having a basic group having a $pK_b$ of 12 or less or a quaternized nitrogen group.

15. A compound according to claim 14, wherein W is $N(R^2)_2$.

16. A compound according to claim 1, of the formula

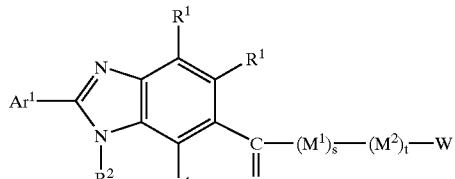

wherein Ar¹, M¹, M², R¹, R², and W are as defined in claim 1; s is an integer from 1 to 5, inclusive; and t is an integer from 1 to 3, inclusive; said compound having a basic group having a $pK_b$ of 12 or less or a quaternary nitrogen group.

17. A compound according to claim 15, wherein W is $N(R^2)_2$.

18. A compound according to claim 1, of the formula

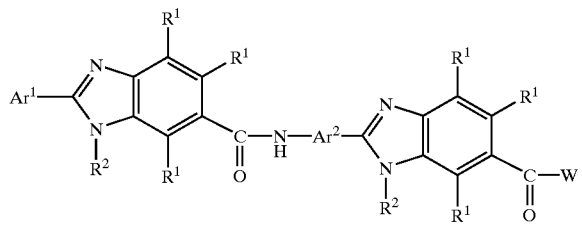

wherein Ar¹, Ar², R¹, R², and W are as defined in claim 1; said compound having a basic group having a $pK_b$ of 12 or less or a quaternary nitrogen group.

19. A compound according to claim 18, wherein W is $N(R^2)_2$.

20. A compound according to claim 1, of the formula

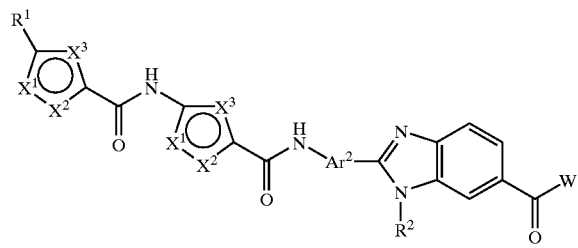

wherein Ar², X¹, X², X³, R¹, R², and W are as defined in claim 1; said compound having a basic group having a $pK_b$ of 12 or less or a quaternary nitrogen group.

21. A compound according to claim 20, wherein W is $N(R^2)_2$.

22. A compound according to claim 20, of the formula

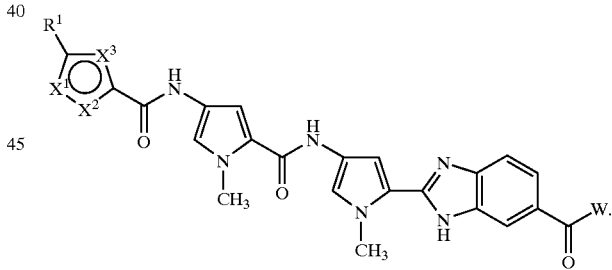

23. A compound according to claim 1, of the formula

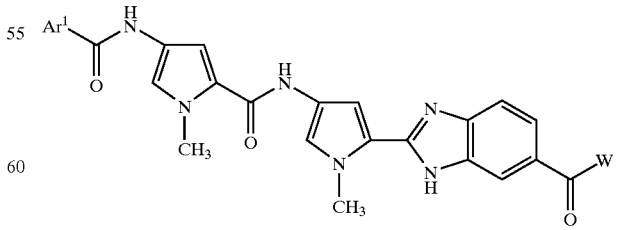

wherein Ar¹ and W are as previously defined and the compound has a basic group having a $pK_b$ of 12 or less or a quaternized nitrogen group.

24. A compound according to claim 23, wherein Ar¹ is

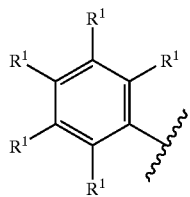

wherein R¹ is as previously defined except that at least one moiety R¹ is halogen.

25. A compound according to claim 24, wherein a moiety R¹ has a basic group having a pK$_b$ of 12 or less or a quaternized nitrogen group.

26. A compound according to claim 24, wherein W is N(R²)$_2$; N(R²)$_2$ having a basic group having a pK$_b$ of 12 or less or a quaternized nitrogen group.

27. A compound according to claim 23, wherein Ar¹ is

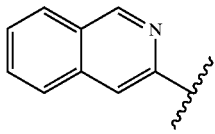

and W is N(R²)$_2$; N(R²)$_2$ having a basic group having a pK$_b$ of 12 or less or a quaternized nitrogen group.

28. A compound according to claim 23, wherein Ar¹ is

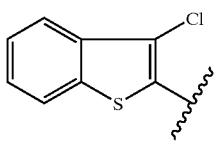

and W is N(R²)$_2$; N(R²)$_2$ having a basic group having a pK$_b$ of 12 or less or a quaternized nitrogen group.

29. A compound according to claim 1, of the formula

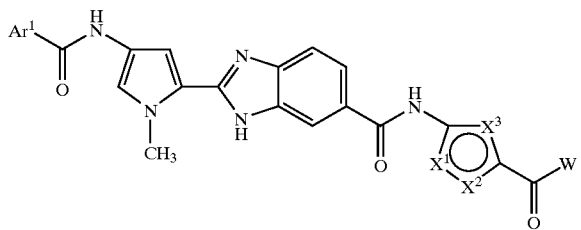

where Ar¹, X¹, X², X³, and W are as previously defined and the compound has a basic group having a pK$_b$ of 12 or less or a quaternized nitrogen group.

30. A compound according to claim 29, wherein Ar¹ is

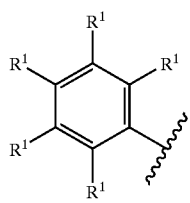

wherein R¹ is as previously defined except that at least one moiety R¹ is halogen.

31. A compound according to claim 30, wherein a moiety R¹ has a basic group having a pK$_b$ of 12 or less or a quaternized nitrogen group.

32. A compound according to claim 30, wherein W is N(R²)$_2$; N(R²)$_2$ having a basic group having a pK$_b$ of 12 or less or a quaternized nitrogen group.

33. A compound according to claim 29, wherein Ar¹ is

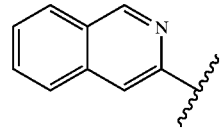

and W is N(R²)$_2$; N(R²)$_2$ having a basic group having a pK$_b$ of 12 or less or a quaternized nitrogen group.

34. A compound according to claim 29, wherein Ar¹ is

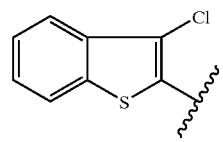

and W is N(R²)$_2$; N(R²)$_2$ having a basic group having a pK$_b$ of 12 or less or a quaternized nitrogen group.

35. A compound according to claim 29, wherein the moiety

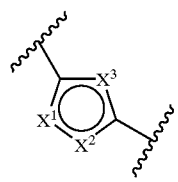

is selected from the group consisting of

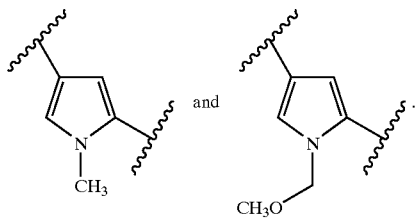

36. A compound according to claim 1, wherein n is an integer from 3 to 12, inclusive.

37. A compound according to claim 1, having a basic group having a pK$_b$ of 12 or less or a quaternized nitrogen.

38. A compound according to claim 1, wherein W is N(R²)$_2$ and N(R²)$_2$ has a basic group having a pK$_b$ of 12 or less or a quaternized nitrogen group.

39. A compound according to claim 1, wherein R¹ is H, halogen, a (C$_1$–C$_5$)alkyl group, a (C$_1$–C$_5$)alkoxy group, hydroxy, or cyano and R² is a (C$_1$–C$_5$)alkyl group.

40. A method of treating a bacterial infection, comprising administering to a patient in need of such treatment an effective amount of a compound according to claim 1.

41. A method according to claim 40, wherein the bacterial infection is an infection by Gram-positive bacteria.

42. A method according to claim 40, wherein the bacteria is MRSA, MRSE, PRSP, or VSE.

* * * * *